(12) United States Patent
Fayard et al.

(10) Patent No.: US 8,933,212 B2
(45) Date of Patent: Jan. 13, 2015

(54) USE OF PROTEASE NEXIN 1 INHIBITORS TO REDUCE METASTASIS

(75) Inventors: Bérengère Fayard, Sierentz (FR); Denis Monard, Füllinsdorf (CH)

(73) Assignee: Novartis Forschungsstiftung Zweigniederlassung Friedrich Miescher Institute for Biomedical Research, Basel (CH)

( * ) Notice: Subject to any disclaimer, the term of this patent is extended or adjusted under 35 U.S.C. 154(b) by 928 days.

(21) Appl. No.: 12/746,214

(22) PCT Filed: Dec. 5, 2008

(86) PCT No.: PCT/EP2008/066879
§ 371 (c)(1),
(2), (4) Date: Jun. 4, 2010

(87) PCT Pub. No.: WO2009/071660
PCT Pub. Date: Jun. 11, 2009

(65) Prior Publication Data
US 2010/0254976 A1 Oct. 7, 2010

(30) Foreign Application Priority Data
Dec. 6, 2007 (EP) ..................... 07122494

(51) Int. Cl.
*C07H 21/04* (2006.01)
(52) U.S. Cl.
USPC ....................................... 536/24.5

(58) Field of Classification Search
None
See application file for complete search history.

(56) References Cited

FOREIGN PATENT DOCUMENTS

WO    WO2008/022806    *  2/2008

OTHER PUBLICATIONS

Sibley et al (Molecular Therapy, 2010, 18:466-476).*
Candia et al. (Cancer Cell International, 6:16, May 2006).*
Stancovski et al. (PNAS, 1991, 88:8691-8695).*
Buchholz, Malte et al, "Serpine2 (Protease Nexin I) Promotes Extracellular Matrix Production and Local Invasion of Pancreatic Tumors in Vivo", Cancer Research, vol. 63, No. 16, pp. 4945-4951 (Aug. 15, 2003).
Candia B et al, "Protease nexin-1 expression is altered in human breast cancer", Cancer Cell International, vol. 6, No. 1, p. 16 (May 31, 2006).
Sliva and Schnierle, "Selective gene silencing by viral delivery of short hairpin RNA," Virology Journal (7): 248, p. 1-11 (2010).
Selbonne, S. et al., "In Vitro and In Vivo Antiangiogenic Properties of the Serpin Protease", Mol. Cell. Biol., vol. 32, No. 8, pp. 1496-1505, (2012).

* cited by examiner

*Primary Examiner* — Laura B Goodard
*Assistant Examiner* — Meera Natarajan
(74) *Attorney, Agent, or Firm* — Hoxie & Associates LLC

(57) ABSTRACT

The present invention relates to a method of inhibiting metastasis comprising the administration of an inhibitor of protease nexin-1 (PN-1), characterized in that said inhibitor is administered at a therapeutical dosage that does not completely inhibit the expression and/or activity of PN-1.

8 Claims, 5 Drawing Sheets

USE OF PROTEASE NEXIN 1 INHIBITORS TO REDUCE METASTASIS

This application is a National Phase application of PCT/EP2008/066879, filed Dec. 5, 2008, which claims benefit of EP 07122494.3, filed Dec. 6, 2007.

FIELD OF THE INVENTION

The present invention relates to the treatment or prevention of metastasis, or formation thereof, using a Protease nexin-1 (PN-1) inhibitor.

BACKGROUND OF THE INVENTION

Protease nexin 1 (PN-1; also known as serpine2, GDN, glia-derived nexin precursor, PI7, protease inhibitor 7, PN1, glial-derived neurite promoting factor, PNI, glial-derived nexin 1, nexin, plasminogen activator inhibitor type 1 member 2, serine (or cysteine) proteinase inhibitor clade E member 2, and serpin peptidase inhibitor clade E member 2) is a secreted 43 kDa protein belonging to the serine protease inhibitors family called serpin. PN-1 can inhibit activity of a broad range of enzymes, such as tissue plasminogen activator (tPA), Urokinase-type plasminogen activator (uPA), thrombin, factor XIa, prostasin.

PN-1 has been originally shown to be involved in development, nerve regeneration and function of NMDA receptor through its inhibitory activity.

In the field of cancer, the role of plasminogen activator inhibitor-1 (PAI-1; also known as serpine1), the other major serine protease inhibitor, has been extensively investigated during the past twenty years. Recently, a few studies recently suggested the importance of PN-1 in cancer. PN-1 has been shown to be overexpressed in malignant breast cancer tumours and has been associated with metastasis in oral squamous carcinoma (Candia et al, 2006, Cancer Cell Int., 6:16; Gao et al, 2007, Oral Oncol., April 27, e-publication). It has also been shown that PN-1 is be able to increase local invasion in pancreatic cancer and PN-1 has been one of the genes identified to be associated with tumour genesis generated by adenovirus 12 (Buchholz et al, 2003, Cancer Res., 63(16): 4945; Guan et al, 2003, Virology, 309(1):114).

As a conclusion, PN-1 seems to be involved and to be associated with malignancy and invasiveness of cancer cells.

Here, the results of the inventors provide additional evidence going in that direction. Indeed, the inventors show that PN-1 via binding to the low-density lipoprotein receptor-related protein-1 (LRP) receptor, can induce increase in secreted MMP-9 level, a metalloproteinase involved in degradation of extracellular matrix, promoting invasion of cancer cells.

The inventors also showed that knock-down of PN-1 in a very metastatic cell line leads to a decrease of matrix metalloproteinase-9 (MMP-9) expression as well as a decrease of metastatic properties of the cells, as shown by in vivo cancer cells injection experiments in the mouse mammary fat pad. These results lead the inventors to consider PN-1 as a pro-invasive and a pro-metastatic agent and a potential target for cancer therapy.

SUMMARY OF THE INVENTION

Hence, according to the prior art, PN-1 seems to be involved and to be associated with malignancy and invasiveness of cancer cells.

The results of the present inventors presented herein provide additional evidence sustaining this association. Indeed, the present inventors show that PN-1 via binding to the LRP receptor, can increase the levels of secreted MMP-9, a metalloproteinase known to be involved in degradation of extracellular matrix, promoting invasion of cancer cells.

Moreover, the inventors also show herein that knock-down of PN-1 in a very metastatic cell line leads to a decrease of MMP-9 expression as well as a decrease of metastatic properties of the cells, as shown by in vivo cancer cells injection experiments in the mouse mammary fat pad.

Surprisingly, the studies of the present inventors demonstrated that a complete inhibition of the expression of PN-1 did not inhibit metastasis whereas a partial inhibition did.

In accordance with these results, the present invention provides a method of inhibiting metastasis comprising the administration of an inhibitor of protease nexin-1 (PN-1), wherein said inhibitor is administered at a therapeutical dosage that does not completely inhibit the expression and/or activity of PN-1. This method of the invention is suitable for any type of cancer. This method of the invention is particularly well suited for cancer forming solid tumours, for instance when the potentially metastising cells are breast tumour cells, prostate carcinoma cells or oral squamous carcinoma cells.

In a preferred embodiment of the invention, the inhibitor is an antibody, a small molecule, an anti-sense molecule or an interfering molecule.

In a particularly preferred embodiment of the invention, the inhibitor and/or its therapeutical dosage does not up-regulate the expression and/or activity of PAI1, as compared to the expression and/or activity of PAI1 in the absence of inhibitor or in non-cancer cells, and/or wherein the inhibitor and/or its therapeutical dosage leads to a down-regulation of the expression and/or activity of MMP-9, as compared to the expression and/or activity of MMP-9 in the absence of inhibitor or in non-cancer cells.

In an embodiment of the invention, the inhibitor and/or its therapeutical dosage inhibits more than 50%, preferably more that 60%, for instance 51%, 52%, 53%, 54%, 55%, 58%, 60%, 61%, 62%, 65%, 68%, 70% or 75%, but less than 90%, preferably less than 80%, for instance 89%, 88%, 85%, 83%, 80%, 78%, 77% or 76%, of the expression and/or activity of PN-1 as compared to the expression and/or activity of PN-1 in the absence of said inhibitor.

The present invention also encompasses a medicament for treating/preventing metastasis. In other words, the present invention encompasses an inhibitor of PN-1 for use as a medicament to treat metastasis, wherein said inhibitor does not completely inhibit the expression and/or activity of PN-1.

The inhibitor of the invention is suitable for any type of cancer and is particularly well suited for the treatment/prevention of metastasis from cancer forming solid tumours, for instance when the potentially metastising cells are breast tumour cells, prostate carcinoma cells or oral squamous carcinoma cells.

In a preferred embodiment of the invention, the inhibitor is an antibody, a small molecule, an anti-sense molecule or an interfering molecule.

In a particularly preferred embodiment of the invention, the inhibitor and/or its therapeutical dosage does not up-regulate the expression and/or activity of PAI1, as compared to the expression and/or activity of PAI1 in the absence of inhibitor or in non-cancer cells, and/or wherein the inhibitor and/or its therapeutical dosage leads to a down-regulation of the expression and/or activity of MMP-9, as compared to the expression and/or activity of MMP-9 in the absence of inhibitor or in non-cancer cells.

These and other aspects of the present invention should be apparent to those skilled in the art, from the teachings herein.

BRIEF DESCRIPTION OF THE DRAWINGS

The following drawings are illustrative of embodiments of the invention and are not meant to limit the scope of the invention as encompassed by the claims.

The four cell lines 67NR, 168FARN, 4T07 and 4T1 were analysed for PN-1 content by Western blot analysis with the anti-PN-1 (4B3). Conditioned media of these cells were analysed for secreted MMP-9 and MMP-2 activity by gelatin zymography (A). 168FARN were incubated during 24 hours with increasing concentrations of recombinant rat PN-1 as indicated and conditioned media were subjected to gelatin zymography for analysis of MMP-9 and MMP-2 content (B, upper panel). 168FARN were incubated during various time with 20 nM of rat recombinant PN-1 and conditioned media were analysed for MMP-9 protein contents by Western Blot (B, lower panel). PN-1 was incubated with thrombin and tPA during 15 min at room temperature to ensure formation of complex serpin/protease. 168FARN were then incubated with PN-1, tPA, complex tPA/PN-1 at the concentration of 20 nM (C, upper panel) or with PN-1, thrombin and thrombin/PN-1 complex at the same concentration (C, lower panel) for 24 hours and conditioned media were harvested for analysis of gelatinases by gelatin zymography. Graphs represent density of MMP-9 band, data being expressed as means +/− SEM on three independent experiments (D).

Figure 2:
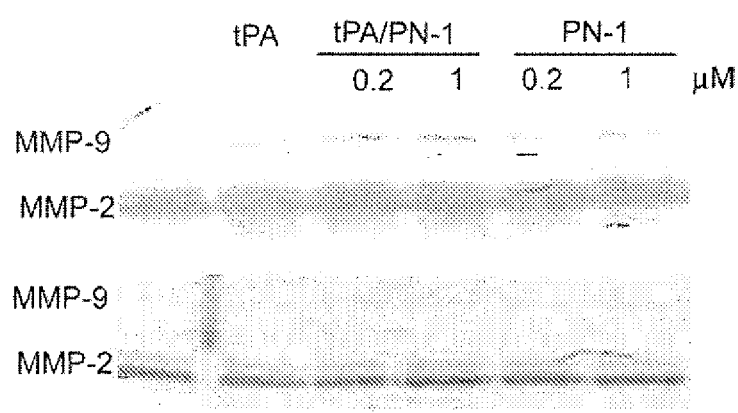

FIG. 2: LRP mediates PN-1 or complex PN-1/tPA effect on the increase of secreted MMP-9.

Wild type MEF (upper panel) and LRP−/− MEF cells were incubated with increasing concentrations of complex tPA/PN-1, PN-1 as indicated or with tPA at 20 nM for 24 h. Conditioned media were analysed for MMP-9 and MM-2 activity by zymography.

Figure 3:
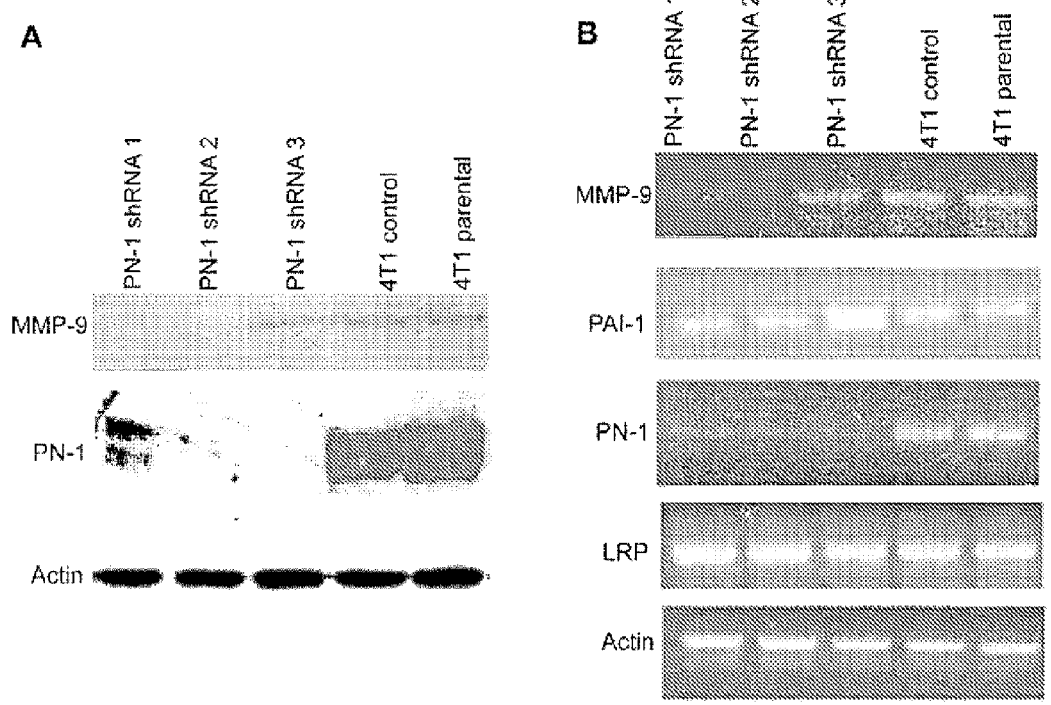

FIG. 3: 4T1 shRNA PN-1 display decrease of MMP-9 expression but efficient PN-1 knock-down leads to PAI-1 up-regulation.

Three representative 4T1-PN-1-knock down clones (1, 22 and 36) were chosen above 20, mock transfected 4T1 clone (as 4T1 control) and untransfected 4T1 cells (as parental 4T1) were analysed for PN-1, PAI-1, MMP-9, LRP expression by Reverse-transcription PCR, actin being used as house keeping gene (right panel). They were also analysed for PN-1 expression by Western Blot and gelatinases activity by zymography (left panel).

FIG. 4: PN-1 knock down leads to decrease of the in vivo metastatic properties of 4T1 cells.

Three 4T1 PN-1 shRNA clones (1, 22, 36) as well as mock transfected 4T1 cells and untransfected 4T1 were injected in the mouse mammary fat pad of Balb/c mice as indicated ($5.10^5$ cells/100 ml/animal, n=11 per group). Tumor size was recorded upon time and represented on the graph (A). After 26 days post-injection, lungs were dissected and fixed in Bouin fixation and photographed (B). Graphs represent means of number of metastases on both lungs, counted under a dissection scope, per group of animal injected with the each 4T1 clone (n=11 per group) (C).

DETAILED DESCRIPTION OF THE INVENTION

Studies of the present inventors have surprisingly demonstrated that a complete inhibition of the expression of PN-1 did not inhibit metastasis whereas a partial inhibition did.

In accordance with these results, the present invention provides a method of inhibiting metastasis comprising the administration of an inhibitor of protease nexin-1 (PN-1), wherein said inhibitor is administered at a therapeutical dosage that does not completely inhibit the expression and/or activity of PN-1. This method of the invention is suitable for any type of cancer. This method of the invention is particularly well suited for cancer forming solid tumours, for instance when the potentially metastising cells are breast tumour cells, prostate carcinoma cells or oral squamous carcinoma cells. Other cancer forming solid tumours for which the methods and inhibitors of the invention would be well suited can be selected from the group consisting of adrenal cortical carcinomas, angiomatoid fibrous histiocytomas (AFH), squamous cell bladder carcinomas, urothelial carcinomas, bone tumours, e.g. adamantinomas, aneurysmal bone cysts, chondroblastomas, chondromas, chondromyxoid fibromas, chondrosarcomas, fibrous dysplasias of the bone, giant cell tumours, osteochondromas or osteosarcomas, breast tumours, e.g. secretory ductal carcinomas, chordomas, clear cell hidradenomas of the skin (CCH), colorectal adenocarcinomas, carcinomas of the gallbladder and extrahepatic bile ducts, combined hepatocellular and cholangiocarcinomas, fibrogenesis imperfecta ossium, pleomorphic salivary gland adenomas head and neck squamous cell carcinomas, chromophobe renal cell carcinomas, clear cell renal cell carcinomas, nephroblastomas (Wilms tumor), papillary renal cell carcinomas, primary renal ASPSCR1-TFE3 t(X;17)(p11;q25) tumors, renal cell carcinomas, laryngeal squamous cell carcinomas, liver adenomas, hepatoblastomas, hepatocellular carcinomas, non-small cell lung carcinomas, small cell lung cancers, malignant melanoma of soft parts, medulloblastomas, meningiomas, neuroblastomas, astrocytic tumours, ependymomas, peripheral nerve sheath tumours, neuroendocrine tumours, e.g. phaeochromocytomas, neurofibromas, oral squamous cell carcinomas, ovarian tumours, e.g. epithelial ovarian tumours, germ cell tumours or sex cord-stromal tumours, pericytomas, pituitary adenomas, posterior uveal melanomas, rhabdoid tumours, skin melanomas, cutaneous benign fibrous histiocytomas, intravenous leiomyomatosis, aggressive angiomyxomas, liposarcomas, myxoid liposarcomas, low grade fibromyxoid sarcomas, soft tissue leiomyosarcomas, biphasic synovial sarcomas, soft tissue chondromas, alveolar soft part sarcomas, clear cell sarcomas, desmoplastic small round cell tumours, elastofibromas, Ewing's tumours, extraskeletal myxoid chondrosarcomas, inflammatory myofibroblastic tumours, lipoblastomas, lipoma, benign lipomatous tumours, liposarcomas, malignant lipomatous tumours, malignant myoepitheliomas, rhabdomyosarcomas, synovial sarcomas, squamous cell cancers, subungual exostosis, germ cell tumours in the testis, spermatocytic seminomas, anaplastic (undifferentiated) carcinomas, oncocytic tumours, papillary carcinomas, carcinomas of the cervix, endometrial carcinomas, leiomyoma as well as vulva and/or vagina tumours.

In a preferred embodiment of the invention, the inhibitor is an antibody, a small molecule, an anti-sense molecule or an interfering molecule.

In a particularly preferred embodiment of the invention, the inhibitor and/or its therapeutical dosage does not up-regulate the expression and/or activity of PAI1, as compared to the expression and/or activity of PAI1 in the absence of inhibitor or in non-cancer cells, and/or wherein the inhibitor and/or its therapeutical dosage leads to a down-regulation of the expression and/or activity of MMP-9, as compared to the expression and/or activity of MMP-9 in the absence of inhibitor or in non-cancer cells.

In an embodiment of the invention, the inhibitor and/or its therapeutical dosage inhibits more than 50%, preferably more that 60%, for instance 51%, 52%, 53%, 54%, 55%, 58%, 60%, 61%, 62%, 65%, 68%, 70% or 75%, but less than 90%, preferably less than 80%, for instance 89%, 88%, 85%, 83%, 80%, 78%, 77% or 76%, of the expression and/or activity of PN-1 as compared to the expression and/or activity of PN-1 in the absence of said inhibitor.

The present invention also encompasses a medicament for treating/preventing metastasis. In other words, the present invention encompasses an inhibitor of PN-1 for use as a medicament to treat metastasis, wherein said inhibitor does not completely inhibit the expression and/or activity of PN-1.

The inhibitor of the invention is suitable for any type of cancer and is particularly well suited for the treatment/prevention of metastasis from cancer forming solid tumours, for instance when the potentially metastising cells are breast tumour cells, prostate carcinoma cells or oral squamous carcinoma cells.

In a preferred embodiment of the invention, the inhibitor is an antibody, a small molecule, an anti-sense molecule or an interfering molecule.

In a particularly preferred embodiment of the invention, the inhibitor and/or its therapeutical dosage does not up-regulate the expression and/or activity of PAI1, as compared to the expression and/or activity of PAI1 in the absence of inhibitor or in non-cancer cells, and/or wherein the inhibitor and/or its therapeutical dosage leads to a down-regulation of the expression and/or activity of MMP-9, as compared to the expression and/or activity of MMP-9 in the absence of inhibitor or in non-cancer cells.

In addition, the present inventors also examined PN-1 expression in several publicly available gene expression datasets of human tumors including breast, bladder, prostate and sarcomas. In breast cancer, PN-1 expression increased in a statistically significant manner with grade. PN-1 levels were also significantly higher in ERα-negative tumors. The correlation between ERα-negativity and high PN-1 expression was found in 5 additional data sets encompassing more than 600 tumors. PN-1 RNA levels were also measured by RT-PCR in 6 breast cancer cell lines. Interestingly, the metastatic ERα negative MDA-MB-231 cell line displayed the highest levels of PN-1, while the ERα-positive MCF-7, T47D, BT-474 and ZR-75-1 cells had relatively low PN-1 levels. The inventors also analyzed PN-1 expression in publicly available data sets of human bladder, prostate and sarcoma tumors. PN-1 expression level was strongly associated with high grade bladder and prostate cancer, and was elevated in high stage sarcomas and bladder tumors. Taken together these in silico results show that elevated PN-1 levels are found in multiple types of human tumors. Moreover, high PN-1 level appears to correlate with clinical parameters predicting poor patient outcome in breast and prostate cancer and with invasive sarcomas and bladder tumors. The present invention thus also encompass the use of PN-1 as a biomarker. For example as a biomarker for the diagnosis and/or prognosis of cancer, e.g. breast, bladder, prostate and sarcoma tumors, wherein the expression and/or concentration of PN-1 is assessed in a sample from a subject and compared to a control, and whereas a high expression correlates with poor prognosis.

These and other aspects of the present invention should be apparent to those skilled in the art, from the teachings herein.

For convenience, the meaning of certain terms and phrases employed in the specification, examples, and appended claims are provided below.

The singular forms "a," ""an," and "the" include plural reference unless the context clearly dictates otherwise.

"Polynucleotide" and "nucleic acid", used interchangeably herein, refer to polymeric forms of nucleotides of any length, either ribonucleotides or deoxyribonucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids, PNA and LNA. Polynucleotides may further comprise genomic DNA, cDNA, or DNA-RNA hybrids.

"Sequence Identity" refers to a degree of similarity or complementarity. There may be partial identity or complete identity. A partially complementary sequence is one that at least partially inhibits an identical sequence from hybridizing to a target polynucleotide; it is referred to using the functional term "substantially identical. "The inhibition of hybridization of the completely complementary sequence to the target sequence may be examined using a hybridization assay (Southern or Northern blot, solution hybridization and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e. g., less than about 30% identity); in the absence of non-specific binding, the probe will not hybridize to the second non-complementary target sequence.

Another way of viewing sequence identity in the context to two nucleic acid or polypeptide sequences includes reference to residues in the two sequences that are the same when aligned for maximum correspondence over a specified region. As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Gene" refers to a polynucleotide sequence that comprises control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

"Expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein.

"Differential expression" refers to both quantitative as well as qualitative differences in the temporal and tissue expression patterns of a gene. For example, a differentially expressed gene may have its expression activated or completely inactivated in normal versus disease conditions. Such a qualitatively regulated gene may exhibit an expression pattern within a given tissue or cell type that is detectable in either control or disease conditions, but is not detectable in both.

"Differentially expressed polynucleotide" refers to a polynucleotide sequence that uniquely identifies a differentially expressed gene so that detection of the differentially expressed polynucleotide in a sample is correlated with the presence of a differentially expressed gene in a sample. "Differentially expressed protein" refers to an amino acid sequence that uniquely identifies a differentially expressed protein so that detection of the differentially expressed protein in a sample is correlated with the presence of a differentially expressed protein in a sample.

"Cancer", "neoplasm", "tumor" and "carcinoma", used interchangeably herein, refer to cells or tissues that exhibit an aberrant growth phenotype characterized by a significant loss of control of cell proliferation.

"Cell type" refers to a cell from a given source (e.g., tissue or organ) or a cell in a given state of differentiation, or a cell associated with a given pathology or genetic makeup.

The phrase "cells that express PN-1" refers to any cell that expresses detectable levels of PN-1. PN-1 protein may be detected using methods such as, but not limited to, quantitative reverse transcription polymerase chain reaction (qRT-PCR), enzyme-linked immunosorbent assay (ELISA), radioimmunoassay (RIA), microarray methods or immunoflourescence. An mRNA encoding PN-1 protein may be detected by Northern blots, polymerase chain reaction (PCR), microarray methods, or in situ hybridization. Other methods for detecting specific polynucleotides or polypeptides are discussed herein and are well known to those skilled in the art.

The phrase "cells that overexpress and/or upregulate PN-1" refers to cells wherein the PN-1 protein or mRNA transcript is expressed at higher levels than in corresponding normal cells. For example, in a cell that overexpresses and/or upregulates PN-1, the mRNA or protein may be produced at levels at least about 20% higher, at least about 25% higher, at least about 30% higher, at least about 35% higher, at least about 40% higher, at least about 45% higher, at least about 50% higher, at least about 55% higher, at least about 60% higher, at least about 65% higher, at least about 70% higher, at least about 75% higher, at least about 80% higher, at least about 85% higher, at least about 90% higher, at least about 95% higher, at least about 100% or more higher, at least about at least about 1.2-fold higher, at least about 1.5-fold higher, at least 1.75-fold higher, at least about 2-fold higher, at least about 5-fold higher, at least about 10-fold higher, or at least about 50-fold or more higher than that of a corresponding normal cell. In a specific embodiment, in a cell that overexpresses and/or upregulates PN-1, the PN-1 mRNA may be produced at levels at least about 1.5-fold higher than that of a corresponding normal cell. In another embodiment of the invention, PN-1 mRNA may be produced at levels at least about 1.75-fold higher than that of a corresponding normal cell. In a further embodiment, PN-1 mRNA may be produced at levels at least about 2.0-fold higher than that of a corresponding normal cell. The comparison may be made between different tissues or between different cells.

"Polypeptide" and "protein", used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

A "fragment of a protein" refers to a protein that is a portion of another protein. For example, fragments of proteins may comprise polypeptides obtained by digesting full-length protein isolated from cultured cells. In one embodiment, a protein fragment comprises at least about 6 amino acids. In another embodiment, the fragment comprises at least about 10 amino acids. In yet another embodiment, the protein fragment comprises at least about 16 amino acids.

An "expression product" or "gene product" is a biomolecule, such as a protein or mRNA, that is produced when a gene in an organism is transcribed or translated or post-translationally modified.

"Host cell" refers to a microorganism, a prokaryotic cell, a eukaryotic cell or cell line cultured as a unicellular entity that may be, or has been, used as a recipient for a recombinant vector or other transfer of polynucleotides, and includes the progeny of the original cell that has been transfected. The progeny of a single cell may not necessarily be completely identical in morphology or in genomic or total DNA complement as the original parent due to natural, accidental, or deliberate mutation.

"PN-1 inhibitor" refers to a molecule that binds to PN-1 polypeptides or polynucleotides. In a specific embodiment of the invention, a PN-1 inhibitor is a polypeptide, i.e., a polypeptide PN-1 inhibitor. Examples of polypeptide PN-1 inhibitors include, but are not limited to, immunoglobulins (antibodies), and functional equivalents thereof, e.g. apatamers, peptides generated by rational design, etc. In another embodiment, a PN-1 inhibitor may comprise a polynucleotide, i.e., a polynucleotide PN-1 inhibitor. In yet another embodiment, a PN-1 inhibitor may comprise a small molecule, i.e., a small molecule PN-1 inhibitor.

In the context of PN-1, the term "functional equivalent" refers to a protein or polynucleotide molecule that possesses functional or structural characteristics that are substantially similar to all or part of the native PN-1 protein or native PN-1-encoding polynucleotides. A functional equivalent of a native PN-1 protein may contain modifications depending on the necessity of such modifications for a specific structure or the performance of a specific function.

The term "functional equivalent" is intended to include the "fragments", "mutants", "derivatives", "alleles", "hybrids", "variants", "analogs", or "chemical derivatives" of native PN-1.

In the context of immunoglobulins, the term "functional equivalent" refers to molecules that exhibit immunological binding properties that are substantially similar to the parent immunoglobulin. "Immunological binding properties" refers to non-covalent specific binding interactions of the type that occurs between an immunoglobulin molecule and an antigen for which the immunoglobulin is specific. Indeed, a functional equivalent of a monoclonal antibody immunoglobulin, for example, may inhibit the binding of the parent monoclonal antibody to its antigen. A functional equivalent may comprise F(ab') 2 fragments, F(ab) molecules, Fv fragments, single chain fragment variable displayed on phage (scFv), single domain antibodies, chimeric antibodies, aptamers or the like so long as the functional equivalent exhibits the characteristics of the parent immunoglobulin.

"Isolated" refers to a polynucleotide, a polypeptide, an immunoglobulin, or a host cell that is in an environment different from that in which the polynucleotide, the polypeptide, the immunoglobulin, or the host cell naturally occurs.

"Substantially purified" refers to a compound that is removed from its natural environment and is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% or more free from other components with which it is naturally associated.

"Diagnosis" and "diagnosing" generally includes a determination of a subject's susceptibility to a disease or disorder, a determination as to whether a subject is presently affected by a disease or disorder, a prognosis of a subject affected by a disease or disorder (e. g., identification of pre-metastatic or metastatic cancerous states, stages of cancer, or responsiveness of cancer to therapy), and therametrics (e. g., monitoring a subject's condition to provide information as to the effect or efficacy of therapy).

"Biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived therefrom and the progeny thereof. The term specifically encompasses a clinical sample, and further includes cells in cell culture, cell supernatants, cell lysates, serum, plasma, urine, amniotic fluid, biological fluids, and tissue samples. The term also encompasses samples that have been manipulated in any way after procurement, such as treatment with reagents, solubilization, or enrichment for certain components.

"Individual", "subject", "host" and "patient", used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Hybridization" refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency.

"Biomolecule" includes polynucleotides and polypeptides.

"Biological activity" refers to the biological behavior and effects of a protein or peptide. The biological activity of a protein may be affected at the cellular level and the molecular level. For example, the biological activity of a protein may be affected by changes at the molecular level. For example, an antisense oligonucleotide may prevent translation of a particular mRNA, thereby inhibiting the biological activity of the protein encoded by the mRNA. In addition, an immunoglobulin may bind to a particular protein and inhibit that protein's biological activity.

"Oligonucleotide" refers to a polynucleotide sequence comprising, for example, from about 10 nucleotides (nt) to about 1000 nt. Oligonucleotides for use in the invention are preferably from about 15 nt to about 150 nt, more preferably from about 150 nt to about 1000 nt in length. The oligonucleotide may be a naturally occurring oligonucleotide or a synthetic oligonucleotide.

"Modified oligonucleotide" and "Modified polynucleotide" refer to oligonucleotides or polynucleotides with one or more chemical modifications at the molecular level of the natural molecular structures of all or any of the bases, sugar moieties, internucleoside phosphate linkages, as well as to molecules having added substitutions or a combination of modifications at these sites. The internucleoside phosphate linkages may be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5'linkages, and combinations of such similar linkages. The phosphodiester linkage may be replaced with a substitute linkage, such as phosphorothioate, methylamino, methylphosphonate, phosphoramidate, and guanidine, and the ribose subunit of the polynucleotides may also be substituted (e. g., hexose phosphodiester; peptide nucleic acids). The modifications may be internal (single or repeated) or at the end(s) of the oligonucleotide molecule, and may include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e. g., 3'-substituted ribonucleotides or deoxyribonucleotide monomers), any of which are bound together via 5'to 3'linkages.

"Biomolecular sequence" or "sequence" refers to all or a portion of a polynucleotide or polypeptide sequence.

The term "microarray" refers generally to the type of genes or proteins represented on a microarray by oligonucleotides (polynucleotide sequences) or protein-capture agents, and where the type of genes or proteins represented on the microarray is dependent on the intended purpose of the microarray (e.g., to monitor expression of human genes or proteins). The oligonucleotides or protein-capture agents on a given microarray may correspond to the same type, category, or group of genes or proteins. Genes or proteins may be considered to be of the same type if they share some common characteristics such as species of origin (e. g., human, mouse, rat); disease state (e.g., cancer); functions (e.g., protein kinases, tumor suppressors); same biological process (e.g., apoptosis, signal transduction, cell cycle regulation, proliferation, differentiation). For example, one microarray type may be a "cancer microarray" in which each of the microarray oligonucleotides or protein-capture agents correspond to a gene or protein associated with a cancer. An "epithelial microarray" may be a microarray of oligonucleotides or protein-capture agents corresponding to unique epithelial genes or proteins. Similarly, a "cell cycle microarray" may be a microarray type in which the oligonucleotides or protein-capture agents correspond to unique genes or proteins associated with the cell cycle.

The term "detectable" refers to a polynucleotide expression pattern which is detectable via the standard techniques of polymerase chain reaction (PCR), reverse transcriptase—(RT) PCR, differential display, and Northern analyses, which are well known to those of skill in the art. Similarly, polypeptide expression patterns may be "detected" via standard techniques including immunoassays such as Western blots.

A "target gene" refers to a polynucleotide, often derived from a biological sample, to which an oligonucleotide probe is designed to specifically hybridize. It is either the presence or absence of the target polynucleotide that is to be detected, or the amount of the target polynucleotide that is to be quantified. The target polynucleotide has a sequence that is complementary to the polynucleotide sequence of the corresponding probe directed to the target. The target polynucleotide may also refer to the specific subsequence of a larger polynucleotide to which the probe is directed or to the overall sequence (e.g., gene or mRNA) whose expression level it is desired to detect.

A "target protein" refers to a polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid may also refer to the specific substructure of a larger protein to which the protein-capture agent is directed or to the overall structure (e. g., gene or mRNA) whose expression level it is desired to detect.

"Complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

"Stringent conditions" refers to conditions under which a probe may hybridize to its target polynucleotide sequence, but to no other sequences. Stringent conditions are sequence-dependent (e. g., longer sequences hybridize specifically at higher temperatures). Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the target sequence hybridize to the target sequence at equilibrium. Typically, stringent conditions will be those in which the salt concentration is at least about 0.01 to about 1.0 M sodium ion concentration (or other salts) at about pH 7.0 to about pH 8.3 and the temperature is at least about 30° C. for short probes (e. g., 10 to 50 nucleotides).

Stringent conditions may also be achieved with the addition of destabilizing agents, such as formamide.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like. The invention also contemplates the use of radioactive isotopes, such as 35S, 32p, 3H, and the like as labels. Colorimetric labels such as colloidal gold or colored glass or plastic (e.g., polystyrene, polypropylene, latex) beads may also be utilized. See, e.g., U.S. Pat. Nos. 4,366,241; 4,277,437; 4,275,149; 3,996,345; 3,939,350; 3,850,752; and 3,817,837.

"Oligonucleotide probe" refers to an oligonucleotide that may recognize a particular target. Depending on context, the term "oligonucleotide probes" refers both to individual oligonucleotide molecules and to a collection of oligonucleotide molecules. In one aspect, an oligonucleotide probe comprises one or more polynucleotide sequences substantially identical to a target polynucleotide sequence or complementary sequence thereof, or portions of the target polynucleotide sequence or complementary sequence thereof.

"Protein-capture agent" refers to a molecule or a multi-molecular complex that can bind a protein to itself. In one embodiment, protein-capture agents bind their binding partners in a substantially specific manner. In one embodiment, protein-capture agents may exhibit a dissociation constant (KD) of less than about 10-6. The protein-capture agent may comprise a biomolecule such as a protein or a polynucleotide. The biomolecule may further comprise a naturally occurring, recombinant, or synthetic biomolecule. Examples of protein-capture agents include immunoglobulins, antigens, receptors, or other proteins, or portions or fragments thereof. Furthermore, protein-capture agents are understood not to be limited to agents that only interact with their binding partners through noncovalent interactions.

Rather, protein-capture agents may also become covalently attached to the proteins with which they bind. For example, the protein-capture agent may be photocrosslinked to its binding partner following binding.

A "small molecule" comprises a compound or molecular complex, either synthetic, naturally derived, or partially synthetic, composed of carbon, hydrogen, oxygen, and nitrogen, which may also contain other elements, and which may have a molecular weight of less than about 15,000, less than about 14,000, less than about 13,000, less than about 12,000, less than about 11,000, less than about 10,000, less than about 9,000, less than about 8,000, less than about 7,000, less than about 6,000, less than about 5,000, less than about 4,000, less than about 3,000, less than about 2,000, less than about 1,000, less than about 900, less than about 800, less than about 700, less than about 600, less than about 500, less than about 400, less than about 300, less than about 200, or less than about 100.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

"BLAST" refers to Basic Local Alignment Search Tool, a technique for detecting ungapped sub-sequences that match a given query sequence.

"BLASTP" is a BLAST program that compares an amino acid query sequence against a protein sequence database. "BLASTX" is a BLAST program that compares the six-frame conceptual translation products of a nucleotide query sequence (both strands) against a protein sequence database.

A "cds" is used in a GenBank DNA sequence entry to refer to the coding sequence. A coding sequence is a sub-sequence of a DNA sequence that is surmised to encode a gene.

A "consensus" or "contig sequence", as understood herein, is a group of assembled overlapping sequences, particularly between sequences in one or more of the databases of the invention.

"PN-1" refers to serpine2 or serine (or cysteine) proteinase inhibitor, clade E, member 2. PN-1 is alternatively known to those skilled in the art as nexin; plasminogen activator inhibitor type 1, member 2; protease nexin 1 (PN1); protease inhibitor (PI7); and glia-derived nexin or glia-derived neurite promoting factor (GDN). See Crisp et al. J. BIOL. CHEM. 277 (49): 47285-91 (2002); Strausberg et al. PROC. NATL. ACAD. Sci. USA 99 (26): 16899-903 (2002); Carter et al. GENOMICS 27 (1): 196-99 (1995); McGrogan et al. BIOTECH. 6: 172-177 (1998); Somer et al. BIOCHEM. 26 (20): 6407-10 (1987); Gloor et al. CELL 47 (5): 687-93 (1986). PN-1 is assigned to locus NM006216 in the GenBank database, ID 5270 in the LocusLink and EntrezGene Databases, ID Hs. 21858 in the UniGene database, and ID 177010 in the On-line Mendelian Inheritance in Man (OMIM) database.

The terms "prognosis" and "prognose" refer to the act or art of foretelling the course of a disease. Additionally, the terms refer to the prospect of survival and recovery from a disease as anticipated from the usual course of that disease or indicated by special features of the individual case. Further, the terms refer to the art or act of identifying a disease from its signs and symptoms.

The terms "indicator" or "prognostic indicator" refer to anything that may serve as, or relate to, a ground or basis for a prognosis. These terms further refer to any grounds or basis of a differential diagnosis, including the results of testing and characterization of gene expression as described herein, and the distinguishing of a disease or condition from others presenting similar symptoms. Additionally, the terms "indicator" or "prognostic indicator" refer to any grounds or basis, including the results of testing and characterization of gene expression as described herein, which may be used to distinguish the probable course of a malignant disease.

"PN-1 inhibitors" are molecules which inhibit the expression and/or activity of PN-1 and include immunoglobulins and functional equivalents of immunoglobulins that specifically bind to PN-1 polypeptides.

The terms "immunoglobulin" and "antibody" are used interchangeably and in their broadest sense herein. Thus, they encompass intact monoclonal antibodies, polyclonal antibodies, multispecific antibodies (e. g., bispecific antibodies) formed from at least two intact antibodies, and antibody fragments, so long as they exhibit the desired biological activity. In one embodiment, the subject immunoglobulins comprise at least one human constant domain. In another embodiment, the PN-1 immunoglobulins comprise a constant domain that exhibits at least about 90-95% sequence identity with a human constant domain and yet retains human effector function. An immunoglobulin PN-1 inhibitor or functional equivalent thereof may be human, chimeric, humanized, murine, CDR-grafted, phage-displayed, bacteria-displayed, yeast-displayed, transgenic-mouse produced, mutagenized, and randomized.

In a specific embodiment, the immunoglobulin PN-1 inhibitor or functional equivalent thereof binds an epitope of PN-1 as expressed in a cancer cell.

The terms "antibody" and "immunoglobulin "cover fully assembled antibodies and antibody fragments that can bind antigen (e.g., Fab', F'(ab) 2, Fv, single chain antibodies, diabodies), including recombinant antibodies and antibody fragments. Preferably, the immunoglobulins or antibodies are chimeric, human, or humanized.

The variable domains of the heavy and light chain recognize or bind to a particular epitope of a cognate antigen. The term "epitope" is used to refer to the specific binding sites or antigenic determinant on an antigen that the variable end of the immunoglobulin binds. Epitopes can be linear, i.e., be composed of a sequence of amino acid residues found in the primary PN-1 sequence. Epitopes also can be conformational, such that an immunoglobulin recognizes a 3-D structure found on a folded PN-1 molecule. Epitopes can also be a combination of linear and conformational elements. Further, carbohydrate portions of a molecule, as expressed by the target bearing tumor cells can also be epitopes.

Immunoglobulins are said to be "specifically binding" if: 1) they exhibit a threshold level of binding activity, and/or 2) they do not significantly cross-react with known related polypeptide molecules. The binding affinity of an immunoglobulin can be readily determined by one of ordinary skill in the art, for example, by Scatchard analysis (Scatchard, Ann. NY Acad. Sci. 51: 660-672,1949).

In some embodiments, the immunoglobulins of the present invention bind to PN-1 at least $10^3$, more preferably at least $10^4$, more preferably at least $10^5$, and even more preferably at least $10^6$ fold higher than to other proteins.

Immunoglobulins of the invention may be polyclonal or monoclonal, and may be produced by any of the well known methods in this art.

Polyclonal antibodies are preferably raised in animals by multiple subcutaneous (sc), intraperitoneal (ip) or intramuscular (im) injections of the relevant antigen and an adjuvant. It may be useful to conjugate the relevant antigen to a protein that is immunogenic in the species to be immunized, In addition, aggregating agents such as alum are suitably used to enhance the immune response.

The term "monoclonal antibody" refers to an antibody obtained from a population of substantially homogeneous antibodies. Monoclonal antibodies are highly specific, being directed against a single antigenic site. Furthermore, in contrast to polyclonal antibody preparations that typically include different antibodies directed against different determinants, each monoclonal antibody is directed against a single determinant on the antigen.

In addition to their specificity, monoclonal antibodies are advantageous in that they may be synthesized while uncontaminated by other immunoglobulins. For example, monoclonal antibodies may be produced by the hybridoma method or by recombinant DNA methods. Monoclonal antibody PN-1 agents also may be isolated from phage antibody libraries.

PN-1-binding immunoglobulins or antibodies can be "chimeric" in the sense that a variable region can come from a one species, such as a rodent, and the constant region can be from a second species, such as a human.

"Humanized" forms of non-human PN-1-binding antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody.

In general, the humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. In one embodiment, humanized antibodies comprise a humanized FR that exhibits at least 65% sequence identity with an acceptor (non-human) FR, e.g., murine FR. The humanized antibody also may comprise at least a portion of an immunoglobulin constant region (Fc), particularly a human immunoglobulin.

Methods for humanizing non-human antibodies have been described in the art. Preferably, a humanized antibody has one or more amino acid residues introduced into it from a source, which is non-human. These non-human amino acid residues are often referred to as "import" residues, which are typically taken from an "import" variable domain. Humanization may be essentially performed by substituting hypervariable region sequences for the corresponding sequences of a human antibody. Accordingly, such humanized antibodies are chimeric wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies. The choice of human variable domains, both light and heavy, to be used in making the humanized antibodies is very important to reduce antigenicity.

Other methods generally involve conferring donor CDR binding affinity onto an antibody acceptor variable region framework. One method involves simultaneously grafting and optimizing the binding affinity of a variable region binding fragment. Another method relates to optimizing the binding affinity of an antibody variable region.

"Antibody fragments" comprise a portion of an intact antibody, preferably the antigen-binding or variable region thereof. Examples of antibody fragments include Fab, Fab', F(ab') 2, Fv fragments, diabodies, linear antibodies, single-chain antibody molecules, and multispecific antibodies formed from antibody fragments.

Papain digestion of antibodies produces two identical antigen-binding fragments, called "Fab" fragments, each with a single antigen-binding site, and a residual "Fc" fragment. The Fab fragments also contain the constant domain of the light chain and the first constant domain (CHI) of the heavy chain.

Pepsin treatment yields an F(ab') 2 fragment that has two antigen-binding sites and is still capable of crosslinking antigen. Fab' fragments differ from Fab fragments by the addition of a few residues at the carboxy terminus of the heavy chain CHI domain including one or more cysteines from the antibody hinge region.

Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are well known in the art.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer.

Collectively, the six hypervariable regions confer antigen binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments comprise the VH and VL domains of antibody, wherein these domains are present in a single polypeptide chain. The Fv polypeptide may further comprise a polypeptide linker between the VH and VL domains that enables the scFv to form the desired structure for antigen binding. See PLUCKTHUN, 113 THE PHARMACOLOGY OF MONOCLONAL ANTIBODIES 269-315 (Rosenburg and Moore eds. 1994). See also WO 93/16185; U.S. Pat. Nos. 5,587,458 and 5,571,894.

Various techniques have been developed for the production of antibody fragments. Traditionally, these fragments were derived via proteolytic digestion of intact antibodies. However, these fragments may now be produced directly by recombinant host cells.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Furthermore, antibodies can be utilized to generate anti-idiotype antibodies that "mimic" polypeptides using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide and/or to bind its ligands/receptors, and thereby block its biological activity.

Polynucleotides encoding antibodies, comprising a nucleotide sequence encoding an antibody are also encompassed. These polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and io ligating of those oligonucleotides, and then amplification of the ligated oligonucleotides by PCR.

The amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polymicleotide are encompassed by the present description and within the skill of the art.

Anti-PN-1 antibodies may be employed in their "naked" or unconjugated form, or may have other agents conjugated to them.

For examples the antibodies may be in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, and the like. Procedures for accomplishing such labeling are well known in the art.

Bispecific antibodies of the invention are small antibody fragments with two antigen-binding sites. Each fragment comprises a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen binding sites. Methods for making bispecific antibodies are well known in the art. Traditional production of full length bispecific antibodies is based on the coexpression of two immunoglobulin heavy chain-light chain pairs, where the two chains have different specificities.

In another approach, antibody variable domains with the desired binding specificities (antibody-antigen combining sites) may be fused to immunoglobulin constant domain sequences. Specifically, the variable domains are fused with an immunoglobulin heavy chain constant domain, comprising at least part of the hinge, CH2, and CH3 regions. In one embodiment, the fusion protein comprises the first heavy-chain constant region (CHI) because it contains the site necessary for light chain binding. Polynucleotides encoding the immunoglobulin heavy chain fusions and, if desired, the immunoglobulin light chain, may be inserted into separate expression vectors and co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Bispecific antibodies also have been produced using leucine zippers and single-chain Fv (sFv) dimers.

In another embodiment, a PN-1 inhibitor may be a peptide generated by rational design or by phage display. For example, the peptide may be a "CDR mimic" or immunoglobulin analogue based on the CDRs of an immunoglobulin.

Polynucleotide PN-1 inhibitors may comprise one or more oligonucleotide probes. In the context of this invention, the term "oligonucleotide" refers to an oligomer or polymer of ribonucleic acid (RNA) or deoxyribonucleic acid (DNA) or variants thereof. Oligonucleotides may comprise naturally occurring nucleotides, sugars and covalent internucleoside (backbone) linkages as well as oligonucleotides having non-naturally occurring portions that function similarly. Such modified or substituted oligonucleotides possess desirable properties such as, for example, enhanced cellular uptake, enhanced affinity for polynucleotide target and increased stability in the presence of nucleases.

In general, oligonucleotide probes specifically hybridize with one or more polynucleotides encoding PN-1. With these target sites in mind, oligonucleotide probes that are sufficiently complementary to the target PN-1 polynucleotides must be chosen. There must be a sufficient degree of complementarity or precise pairing such that stable and specific binding occurs between the oligonucleotide and the PN-1 polynucleotide target. Importantly, the sequence of an oligonucleotide PN-1 probe need not be 100% complementary to that of its target PN-1 polynucleotide to be specifically hybridizable.

Probes specific to the PN-1 polynucleotides may be generated using the PN-1 polynucleotide sequences. Probes may be designed based on a subset of the PN-1 polynucleotide sequence, such as part of the coding region, flanking region, or a conserved motif.

A PN-1 probe may comprise a contiguous sequence of nucleotides at least about 10 nt, at least about 12 nt, at least about 15 nt, at least about 16 nt, at least about 18 nt, at least about 20 nt, at least about 22 nt, at least about 24 nt, or at least about 25 nt in length that uniquely identifies a polynucleotide sequence.

Moreover, a PN-1 probe may be at least about 30 nt, at least about 35 nt, at least about 40 nt, at least about 45, at least about 50 nt, at least about 55nt, at least about 60 nt, at least about 70 nt, at least about 75 nt, at least about 80 nt, at least about 85 nt, at least about 90 nt, at least about 95 nt, at least about 100 nt, at least about 150 nt, at least about 200 nt, at least about 250 nt, at least about 300 nt, at least about 350 nt, at least about 400 nt, at least about 450 nt, at least about 500 nt, at least about 550 nt, at least about 600 nt, at least about 650 nt, at least about 700 nt, at least about 750 nt, at least about 800 nt, at least about 900 nt, at least about 950 nt, or at least about 1000 nt.

Generally, a PN-1 probe may be at least about 10 nt to at least about 20 nt in length, at least about 50 nt to at least about 100 nt in length, at least about 10 to at least about 100 nt, or at least about 10 to at least about 1000 nt in length.

A PN-1 probe may exhibit less than about 99.99%, less than about 99.9%, less than about 99%, less than about 98%, less than about 97%, less than about 96%, less than about 95%, less than about 94, less than about 93%, less than about 92%, less than about 91%, less than about 90%, less than about 88%, less than about 85%, less than about 83%, less than about 80%, less than about 75%, less than about 70%, or less than about 65% sequence identity to any contiguous nucleotide sequence of more than about 15 nt. Furthermore, the probes may be synthesized chemically or may be generated from longer polynucleotides using restriction enzymes. In addition, the probes may be labeled with a radioactive, biotinylated, or fluorescent tag [0117] Polynucleotides generally comprising at least 12 contiguous nt of a PN-1 polynucleotide are used for probes. A probe that hybridizes specifically to a PN-1 polynucleotide disclosed herein should provide a detection signal at least about 0.3-fold higher, at least about 0.5-fold higher, at least about 0.7-fold higher, at least about 0.8-fold higher, at least about 0.9-fold higher, at least about 1.0-fold higher, at least about 1.2-fold higher, at least about 1.4-fold higher, at least about 1.5-fold, at least about 1.6-fold higher, at least about 1.8-fold higher, at least about 2-fold higher, at least about 2. 5-fold higher, at least about 3.0-fold higher, at least about 3.5-fold higher, at least about 4.0-fold higher, at least about 4.5-fold higher, at least about 5-fold higher, at least about 10-fold higher, or at least about 20-fold or more higher than the background hybridization provided with other unrelated sequences.

Figure 1:
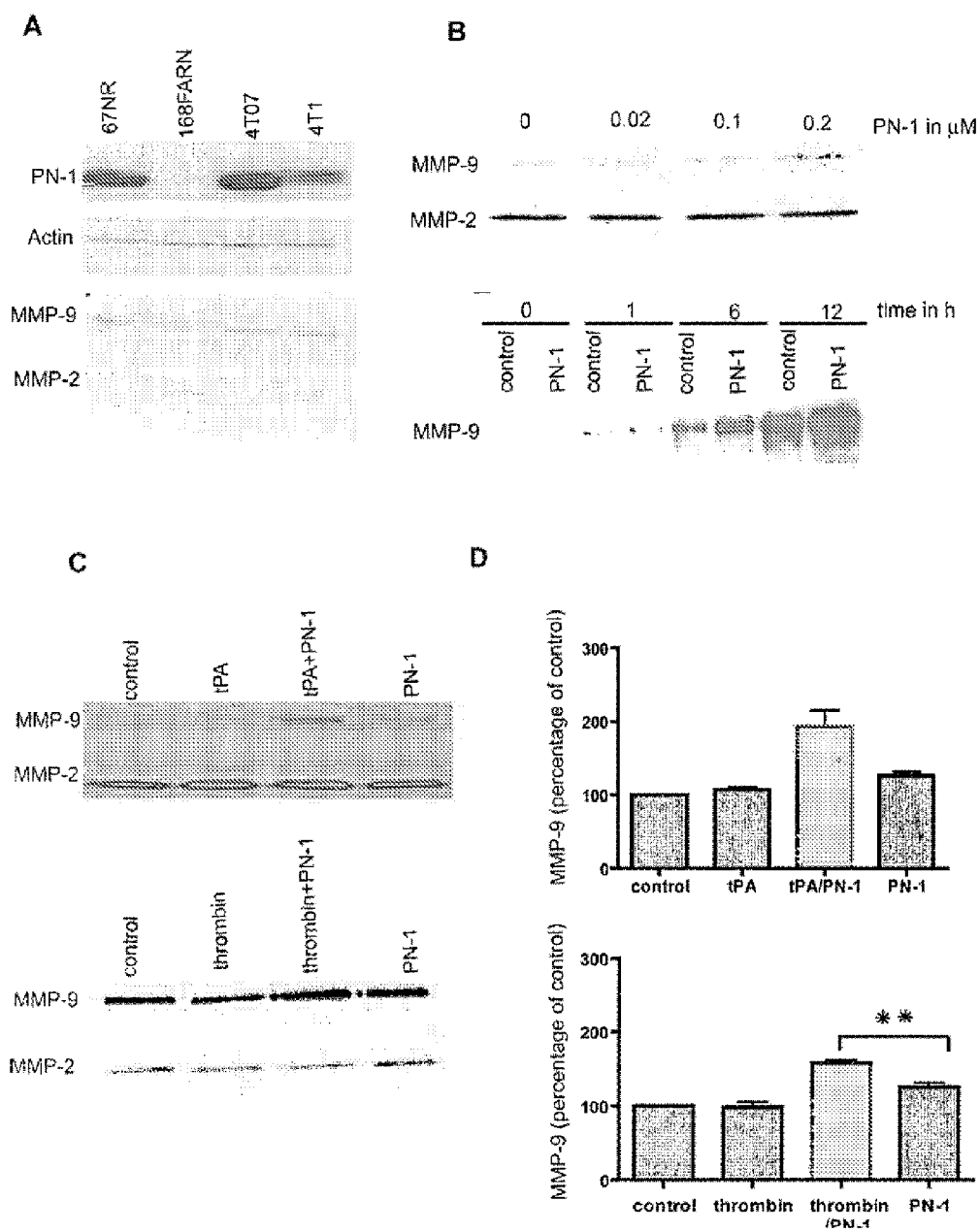
FIG. 1: PN-1, PN-1/tPA and PN-1/thrombin complexes induced increase of secreted MMP-9 by 168FARN cancer cells.

In addition to the sequences provided herein, PN-1 oligonucleotide probes, as well as oligonucleotide probes specific for other relevant genes, may be selected from a number of sources including polynucleotide databases such as GenBank, Unigen, HomoloGene, RefSeq, dbEST, and dbSNP. Wheeler et al., 29 NUCL. ACIDS RES. 11 16 (2001). More specifically, PN-1 oligonucleotide probes may be selected from FIG. 1, FIG. 2, locus NM006216 in the GenBank database, ID 5270 in the LocusLink Database, ID Hs. 21858 in the UniGene database, and ID 177010 in the On-line Mendelian Inheritance in Man (OMIM) database.

Generally, the probe is complementary to the reference sequence, preferably unique to the tissue or cell type (e.g., skeletal muscle, neuronal tissue) of interest, and preferably hybridizes with high affinity and specificity, Lockhart et al., 14 NATURE BIOTECHNOL. 1675-80 (1996). In addition, the oligonucleotide probe may represent non-overlapping sequences of the reference sequence, which improves probe redundancy resulting in a reduction in false positive rate and an increased accuracy in target quantitation. Lipshutz et al., 21 NATURE GENET. 20 24 (1999).

Generally, the oligonucleotide probes are generated by standard synthesis chemistries such as phosphoramidite chemistry (U.S. Pat. Nos. 4,980,460; 4,973,679; 4,725,677; 4,458,066; and 4,415,732; Beaucage and Iyer, 48 TETRAHEDRON 2223-2311 (1992)). Alternative chemistries that create non-natural backbone groups, such as phosphorothionate and phosphoroamidate may also be employed.

Preferred polynucleotide PN-1 inhibitors are interefring or antisense molecules. "RNAi" is the process of sequence specific post-transcriptional gene silencing in animals and plants. It uses small interfering RNA molecules (siRNA) that are double-stranded and homologous in sequence to the silenced (target) gene. Hence, sequence specific binding of the siRNA molecule with mRNAs produced by transcription of the target gene allows very specific targeted knockdown of gene expression.

"siRNA" or "small-interfering ribonucleic acid" according to the invention has the meanings known in the art, including the following aspects. The siRNA consists of two strands of ribonucleotides which hybridize along a complementary region under physiological conditions. The strands are normally separate. Because of the two strands have separate roles in a cell, one strand is called the "anti-sense" strand, also known as the "guide" sequence, and is used in the functioning RISC complex to guide it to the correct mRNA for cleavage. This use of "anti-sense", because it relates to an RNA compound, is different from the antisense target DNA compounds referred to elsewhere in this specification. The other strand is known as the "anti-guide" sequence and because it contains the same sequence of nucleotides as the target sequence, it is also known as the sense strand. The strands may be joined by a molecular linker in certain embodiments. The individual ribonucleotides may be unmodified naturally occurring ribonucleotides, unmodified naturally occurring deoxyribonucleotides or they may be chemically modified or synthetic as described elsewhere herein.

For the purpose of the present invention, the terms siRNA and shRNA can be used interchangeably. "shRNA" (short hairpin RNA; short interfering hairpin) contains sense and antisense sequences from a target gene connected by a loop, and is expressed in mammalian cells from a vector by a pol III-type promoter. The shRNA is transported from the nucleus into the cytoplasm, where Dicer processes it. Once in the cell, the shRNA can decrease the expression of a gene with complementary sequences by RNAi.

Preferably, the siRNA molecule is substantially identical with at least a region of the coding sequence of the target gene to enable down-regulation of the gene. Preferably, the degree of identity between the sequence of the siRNA molecule and the targeted region of the gene is at least 60% sequence identity, preferably, at least 75% sequence identity, preferably at least 85% identity; preferably at least 90% identity; preferably at least 95% identity; preferably at least 97% identity; and most preferably, at least 99% identity.

Calculation of percentage identities between different amino acid/polypeptide/nucleic acid sequences may be carried out as follows. A multiple alignment is first generated by the ClustalX program (pairwise parameters: gap opening 10.0, gap extension 0.1, protein matrix Gonnet 250, DNA matrix IUB; multiple parameters: gap opening 10.0, gap extension 0.2, delay divergent sequences 30%, DNA transition weight 0.5, negative matrix off, protein matrix gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesised de novo, or may be native amino acid/polypeptide/nucleic acid sequence, or a derivative thereof. A substantially similar nucleotide sequence will be encoded by a sequence which hybridizes to any of the nucleic acid sequences referred to herein or their complements under stringent conditions. By stringent conditions, we mean the nucleotide hybridises to filter-bound DNA or RNA in 6× sodium chloride/sodium citrate (SSC) at approximately 45° C. followed by at least one wash in 0.2×SSC/0.1% SDS at approximately 5-65° C. Alternatively, a substantially similar polypeptide may differ by at least 1, but less than 5, 10, 20, 50 or 100 amino acids from the peptide sequences according to the present invention Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequences which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine; large non-polar, hydrophobic amino acids include phenylalanine, tryptophan and tyrosine; the polar neutral amino acids include serine, threonine, cysteine, asparagine and glutamine; the positively charged (basic) amino acids include lysine, arginine and histidine; and the negatively charged (acidic) amino acids include aspartic acid and glutamic acid.

The accurate alignment of protein or DNA sequences is a complex process, which has been investigated in detail by a number of researchers. Of particular importance is the trade-off between optimal matching of sequences and the introduction of gaps to obtain such a match. In the case of proteins, the means by which matches are scored is also of significance. The family of PAM matrices (e.g., Dayhoff, M. et al., 1978, Atlas of protein sequence and structure, Natl. Biomed. Res. Found.) and BLOSUM matrices quantify the nature and likelihood of conservative substitutions and are used in multiple alignment algorithms, although other, equally applicable matrices will be known to those skilled in the art. The popular multiple alignment program ClustalW, and its windows version ClustalX (Thompson et al., 1994, Nucleic Acids Research, 22, 4673-4680; Thompson et al., 1997, Nucleic Acids Research, 24, 4876-4882) are efficient ways to generate multiple alignments of proteins and DNA.

Frequently, automatically generated alignments require manual alignment, exploiting the trained user's knowledge of the protein family being studied, e.g., biological knowledge of key conserved sites. One such alignment editor programs is Align (http://www.gwdg.de/dhepper/download/; Hepperle, D., 2001: Multicolor Sequence Alignment Editor. Institute of Freshwater Ecology and Inland Fisheries, 16775 Stechlin, Germany), although others, such as JalView or Cinema are also suitable.

Calculation of percentage identities between proteins occurs during the generation of multiple alignments by Clustal. However, these values need to be recalculated if the alignment has been manually improved, or for the deliberate comparison of two sequences. Programs that calculate this value for pairs of protein sequences within an alignment include PROTDIST within the PHYLIP phylogeny package (Felsenstein; http://evolution.gs.washington.edu/phylip.html) using the "Similarity Table" option as the model for amino acid substitution (P). For DNA/RNA, an identical option exists within the DNADIST program of PHYL1P.

The dsRNA molecules in accordance with the present invention comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. In an embodiment, the RNA molecules of the present invention specifically target one given gene. In order to only target the desired mRNA, the siRNA reagent may have 100% homology to the target mRNA and at least 2 mismatched nucleotides to all other genes present in the cell or organism. Methods to analyze and identify siRNAs with sufficient sequence identity in order to effectively inhibit expression of a specific target sequence are known in the art. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BEST-FIT software program using default parameters (e.g., University of Wisconsin Genetic Computing Group).

The length of the region of the siRNA complementary to the target, in accordance with the present invention, may be from 10 to 100 nucleotides, 12 to 25 nucleotides, 14 to 22 nucleotides or 15, 16, 17 or 18 nucleotides. Where there are mismatches to the corresponding target region, the length of the complementary region is generally required to be somewhat longer. In a preferred embodiment, the inhibitor is a siRNA molecule and comprises between approximately 5 bp and 50 bp, more preferably between 10 bp and 35 bp, even more preferably between 15 bp and 30 bp, and yet still more preferably, between 18 bp and 25 bp. Most preferably, the siRNA molecule comprises more than 20 and less than 23 bp.

Because the siRNA may carry overhanging ends (which may or may not be complementary to the target), or additional nucleotides complementary to itself but not the target gene, the total length of each separate strand of siRNA may be 10 to 100 nucleotides, 15 to 49 nucleotides, 17 to 30 nucleotides or 19 to 25 nucleotides.

The phrase "each strand is 49 nucleotides or less" means the total number of consecutive nucleotides in the strand, including all modified or unmodified nucleotides, but not including any chemical moieties which may be added to the 3' or 5' end of the strand. Short chemical moieties inserted into the strand are not counted, but a chemical linker designed to join two separate strands is not considered to create consecutive nucleotides.

The phrase "a 1 to 6 nucleotide overhang on at least one of the 5' end or 3' end" refers to the architecture of the complementary siRNA that forms from two separate strands under physiological conditions. If the terminal nucleotides are part of the double-stranded region of the siRNA, the siRNA is considered blunt ended. If one or more nucleotides are unpaired on an end, an overhang is created. The overhang length is measured by the number of overhanging nucleotides. The overhanging nucleotides can be either on the 5' end or 3' end of either strand.

The siRNA according to the present invention display a high in vivo stability and may be particularly suitable for oral delivery by including at least one modified nucleotide in at least one of the strands. Thus the siRNA according to the present invention contains at least one modified or non-natural ribonucleotide. A lengthy description of many known chemical modifications are set out in published PCT patent application WO 200370918. Suitable modifications for delivery include chemical modifications can be selected from among:

a) a 3' cap;
b) a 5' cap,
c) a modified internucleoside linkage; or
d) a modified sugar or base moiety.

Suitable modifications include, but are not limited to modifications to the sugar moiety (i.e. the 2' position of the sugar moiety, such as for instance 2'-O-(2-methoxyethyl) or 2'-MOE) (Martin et al., Helv. Chim. Acta, 1995, 78, 486-504) i.e., an alkoxyalkoxy group) or the base moiety (i.e. a non-natural or modified base which maintains ability to pair with another specific base in an alternate nucleotide chain). Other modifications include so-called 'backbone' modifications including, but not limited to, replacing the phosphoester group (connecting adjacent ribonucleotides) with for instance phosphorothioates, chiral phosphorothioates or phosphorodithioates.

End modifications sometimes referred to herein as 3' caps or 5' caps may be of significance. Caps may consist of simply adding additional nucleotides, such as "T-T" which has been found to confer stability on an siRNA. Caps may consist of more complex chemistries which are known to those skilled in the art.

Design of a suitable siRNA molecule is a complicated process, and involves very carefully analysing the sequence of the target mRNA molecule. On exemplary method for the design of siRNA is illustrated in WO2005/059132. Then, using considerable inventive endeavour, the inventors have to choose a defined sequence of siRNA which has a certain composition of nucleotide bases, which would have the required affinity and also stability to cause the RNA interference.

The siRNA molecule may be either synthesised de novo, or produced by a micro-organism. For example, the siRNA molecule may be produced by bacteria, for example, E. coli. Methods for the synthesis of siRNA, including siRNA containing at least one modified or non-natural ribonucleotides are well known and readily available to those of skill in the art. For example, a variety of synthetic chemistries are set out in published PCT patent applications WO2005021749 and WO200370918, both incorporated herein by reference. The reaction may be carried out in solution or, preferably, on solid phase or by using polymer supported reagents, followed by combining the synthesized RNA strands under conditions, wherein a siRNA molecule is formed, which is capable of mediating RNAi.

It should be appreciated that siNAs (small interfering nucleic acids) may comprise uracil (siRNA) or thyrimidine (siDNA). Accordingly the nucleotides U and T, as referred to above, may be interchanged. However it is preferred that siRNA is used.

Gene-silencing molecules, i.e. inhibitors, used according to the invention are preferably nucleic acids (e.g. siRNA or antisense or ribozymes). Such molecules may (but not necessarily) be ones, which become incorporated in the DNA of cells of the subject being treated. Undifferentiated cells may be stably transformed with the gene-silencing molecule leading to the production of genetically modified daughter cells (in which case regulation of expression in the subject may be required, e.g. with specific transcription factors, or gene activators).

The gene-silencing molecule may be either synthesised de novo, and introduced in sufficient amounts to induce gene-silencing (e.g. by RNA interference) in the target cell. Alternatively, the molecule may be produced by a micro-organism, for example, E. coli, and then introduced in sufficient amounts to induce gene silencing in the target cell.

The molecule may be produced by a vector harbouring a nucleic acid that encodes the gene-silencing sequence. The vector may comprise elements capable of controlling and/or enhancing expression of the nucleic acid. The vector may be a recombinant vector. The vector may for example comprise plasmid, cosmid, phage, or virus DNA. In addition to, or instead of using the vector to synthesise the gene-silencing molecule, the vector may be used as a delivery system for transforming a target cell with the gene silencing sequence.

The recombinant vector may also include other functional elements. For instance, recombinant vectors can be designed such that the vector will autonomously replicate in the target cell. In this case, elements that induce nucleic acid replication may be required in the recombinant vector. Alternatively, the recombinant vector may be designed such that the vector and recombinant nucleic acid molecule integrates into the genome of a target cell. In this case nucleic acid sequences, which favour targeted integration (e.g. by homologous recombination) are desirable. Recombinant vectors may also have DNA coding for genes that may be used as selectable markers in the cloning process.

The recombinant vector may also comprise a promoter or regulator or enhancer to control expression of the nucleic acid as required. Tissue specific promoter/enhancer elements may be used to regulate expression of the nucleic acid in specific cell types, for example, endothelial cells. The promoter may be constitutive or inducible.

Alternatively, the gene silencing molecule may be administered to a target cell or tissue in a subject with or without it being incorporated in a vector. For instance, the molecule may be incorporated within a liposome or virus particle (e.g. a retrovirus, herpes virus, pox virus, vaccina virus, adenovirus, lentivirus and the like).

Alternatively a "naked" siRNA or antisense molecule may be inserted into a subject's cells by a suitable means e.g. direct endocytotic uptake.

The gene silencing molecule may also be transferred to the cells of a subject to be treated by either transfection, infection, microinjection, cell fusion, protoplast fusion or ballistic bombardment. For example, transfer may be by: ballistic transfection with coated gold particles; liposomes containing an siNA molecule; viral vectors comprising a gene silencing sequence or means of providing direct nucleic acid uptake (e.g. endocytosis) by application of the gene silencing molecule directly.

In a preferred embodiment of the present invention siNA molecules may be delivered to a target cell (whether in a vector or "naked") and may then rely upon the host cell to be replicated and thereby reach therapeutically effective levels. When this is the case the siNA is preferably incorporated in an expression cassette that will enable the siNA to be transcribed in the cell and then interfere with translation (by inducing destruction of the endogenous mRNA coding the targeted gene product).

Inhibitors according to any embodiment of the present invention may be used in a monotherapy (e.g. use of siRNAs alone). However it will be appreciated that the inhibitors may be used as an adjunct, or in combination with other therapies.

Small molecules constitute another type of PN-1 inhibitors. In general, small molecules comprise a compound or molecular complex, either synthetic, naturally derived, or partially synthetic, composed of carbon, hydrogen, oxygen, and nitrogen, which may also contain other elements, and which may have a molecular weight of less than about 15,000, less than about 14,000, less than about 13,000, less than about 12,000, less than about 11,000, less than about 10,000, less than about 9,000, less than about 8,000, less than about 7,000, less than about 6,000, less than about 5,000, less than about 4,000, less than about 3,000, less than about 2,000, less than about 1,000, less than about 900, less than about 800, less than about 700, less than about 600, less than about 500, less than about 400, less than about 300, less than about 200, or less than about 100.

PN-1 inhibitors can be easily identified using the methods described in WO-A-03/046006.

PN-1 inhibitors generally are "substantially purified" meaning separated and/or recovered from a component of their natural environment.

Contaminant components of its natural environment are materials that would interfere with therapeutical uses for the PN-1 inhibitor, and may include enzymes, hormones, and other proteinaceous or nonproteinaceous solutes. Ordinarily, an isolated agent will be prepared by at least one purification step. In one embodiment, the agent is purified to at least about 60%, at least about 65%, at least about 70%, at least about 75%, at least about 80%, at least about 85%, at least about 88%, at least about 90%, at least about 92%, at least about 95%, at least about 97%, at least about 98%, at least about 99%, at least about 99.9%, or at least about 99.99% by weight of PN-1 inhibitor.

Amino acid sequence variants of the polypeptide PN-1 inhibitors of the invention may be prepared by introducing appropriate nucleotide changes into the polynucleotide that encodes the polypeptide PN-1 inhibitor or by peptide synthesis. Such modifications include, for example, deletions from, and/or insertions into and/or substitutions of, residues within the amino acid sequences of the polypeptide PN-1 inhibitor. Any combination of deletions, insertions, and substitutions may be made to arrive at the final construct, provided that the final construct decreases or inhibits the proliferation of a cancer characterized by overexpression and/or upregulation of PN-1.

Amino acid sequence insertions include amino-terminal and/or carboxyl-terminal fusions ranging in length from one residue to polypeptides containing a hundred or more residues, as well as intrasequence insertions of single or multiple amino acid residues. Examples of terminal insertions include a polypeptide PN-1 inhibitor with an N-terminal methionyl residue or the polypeptide PN-1 inhibitor fused to a cytotoxic polypeptide. Other insertional variants of the polypeptide PN-1 inhibitor molecule include the fusion to the N-or C-terminus of the binding partner of an enzyme, or a polypeptide that increases the serum half-life of the inhibitor.

Another type of polypeptide PN-1 inhibitor variant is an amino acid substitution variant. These variants have at least one amino acid residue in the polypeptide PN-1 inhibitor molecule replaced by a different residue. For example, the sites of greatest interest for substitutional mutagenesis of immunoglobulin PN-1 inhibitors include the hypervariable regions, but FR alterations are also contemplated.

A useful method for the identification of certain residues or regions of the polypeptide PN-1 inhibitor that are preferred locations for substitution, i.e., mutagenesis, is alanine scanning mutagenesis. See Cunningham & amp; Wells, 244 SCIENCE 1081-85 (1989). Briefly, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. The amino acid locations demonstrating functional sensitivity to the substitutions are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis may be conducted at the target codon or region and the expressed binding partner variants screened for the desired activity.

Substantial modifications in the biological properties of the PN-1 polypeptide inhibitor can be accomplished by selecting substitutions that differ significantly in their effect on, maintaining (i) the structure of the polypeptide backbone in the area of the substitution, for example, as a sheet or helical conformation, (ii) the charge or hydrophobicity of the molecule at the target site, or (iii) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Non-conservative substitutions will entail exchanging a member of one of these classes for another class. Conservative substitutions involve exchanging of amino acids within the same class.

Any cysteine residue not involved in maintaining the proper conformation of the polypeptide PN-1 inhibitor also may be substituted, generally with serine, to improve the oxidative stability of the molecule and prevent aberrant crosslinking. Conversely, cysteine bond(s) may be added to the inhibitor to improve its stability, particularly where the polypeptide PN-1 inhibitor is an immunoglobulin fragment such as an Fv fragment.

Another type of substitutional variant involves substituting one or more hypervariable region residues of a parent immunoglobulin. Generally, the resulting variant(s), i.e., functional equivalents as defined above, selected for further development will have improved biological properties relative to the parent immunoglobulin from which they are generated. A convenient way for generating such substitutional variants is by affinity maturation using phage display. Briefly, several hypervariable region sites (e.g., 6-7 sites) are mutated to generate all possible amino substitutions at each site. The immunoglobulin variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine-scanning mutagenesis may be performed to identify hypervariable region residues contributing significantly to antigen binding.

Alternatively, or additionally, it may be beneficial to analyze a crystal structure of the immunoglobulin-antibody complex to identify contact points between the immunoglobulin and antigen. Such contact residues and neighboring residues are candidates for substitution according to the techniques elaborated herein. Once generated, the panel of variants is subjected to screening as described herein and immunoglobulin with superior properties in one or more relevant assays may be selected for further development.

Another type of amino acid variant of the polypeptide PN-1 inhibitor alters the original glycosylation pattern of the polypeptide PN-1 inhibitor. An "altered glycosylation pattern" includes deleting one or more carbohydrate moieties found in the polypeptide PN-1 inhibitor, and/or adding one or more glycosylation sites that are not present in the polypeptide PN-1 inhibitor.

Glycosylation of polypeptides is typically either N-linked or O-linked. N-linked glycosylation refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the inhibitor is conveniently accomplished by altering the amino acid sequence such that it contains one or more of the above-described tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The alteration may also be made by the addition of, or substitution by, one or more serine or threonine residues to the sequence of the original inhibitor.

To increase the serum half life of an immunoglobulin PN-1 inhibitor, one may incorporate a salvage receptor binding epitope into the PN-1 inhibitor (especially an immunoglobulin fragment) as described in, for example, U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Polynucleotide molecules encoding amino acid sequence variants of the polypeptide PN-1 inhibitors are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the polypeptide PN-1 inhibitors.

The term "Metastasis" refers to the spread of cancer cells from one organ or body part to another area of the body, i.e. to the formation of metastases. This movement of tumor growth, i.e. metastasis or the formation of metastases, occurs as cancer cells break off the original tumor and spread e.g. by way of the blood or lymph system. Without wishing to be bound by theory, metastasis is an active process and involves an active breaking from the original tumor, for instance by protease digestion of membranes and or cellular matrices, transport to another site of the body, for instance in the blood circulation or in the lymphatic system, and active implantation at said other area of the body.

"Cancer" is a group of diseases in which cells are aggressive (grow and divide without respect to normal limits), invasive (invade and destroy adjacent tissues), and sometimes metastatic (spread to other locations in the body). These three malignant properties of cancers differentiate them from benign tumors, which are self-limited in their growth and do not invade or metastasize (although some benign tumor types are capable of becoming malignant). Cancer is usually classified according to the tissue from which the cancerous cells originate, as well as the normal cell type they most resemble. These are location and histology, respectively. A definitive diagnosis usually requires the histologic examination of a tissue biopsy specimen by a pathologist, although the initial indication of malignancy can be symptoms or radiographic imaging abnormalities. Most cancers can be treated and some cured, depending on the specific type, location, and stage. Once diagnosed, cancer is usually treated with a combination of surgery, chemotherapy and radiotherapy. Examples of cancers which could from metastasis and could therefore be treated according to the present invention include, but are not limited to, prostate cancer, lung cancer, breast cancer, colorectal cancer, bladder cancer, pancreatic cancer, endometrial cancer, ovarian cancer, and cutaneous melanoma.

Cancer forming solid tumours for which the methods and inhibitors of the invention is well suited can be selected from the group consisting of adrenal cortical carcinomas, angiomatoid fibrous histiocytomas (AFH), squamous cell bladder carcinomas, urothelial carcinomas, bone tumours, e.g. adamantinomas, aneurysmal bone cysts, chondroblastomas, chondromas, chondromyxoid fibromas, chondrosarcomas, fibrous dysplasias of the bone, giant cell tumours, osteochondromas or osteosarcomas, breast tumours, e.g. secretory ductal carcinomas, chordomas, clear cell hidradenomas of the skin (CCH), colorectal adenocarcinomas, carcinomas of the gallbladder and extrahepatic bile ducts, combined hepatocellular and cholangiocarcinomas, fibrogenesis imperfecta ossium, pleomorphic salivary gland adenomas head and neck squamous cell carcinomas, chromophobe renal cell carcinomas, clear cell renal cell carcinomas, nephroblastomas (Wilms tumor), papillary renal cell carcinomas, primary renal ASPSCR1-TFE3 t(X;17)(p11;q25) tumors, renal cell carcinomas, laryngeal squamous cell carcinomas, liver adenomas, hepatoblastomas, hepatocellular carcinomas, non-small cell lung carcinomas, small cell lung cancers, malignant melanoma of soft parts, medulloblastomas, meningiomas, neuroblastomas, astrocytic tumours, ependymomas, peripheral nerve sheath tumours, neuroendocrine tumours, e.g. phaeochromocytomas, neurofibromas, oral squamous cell carcinomas, ovarian tumours, e.g. epithelial ovarian tumours, germ cell tumours or sex cord-stromal tumours, pericytomas, pituitary adenomas, posterior uveal melanomas, rhabdoid tumours, skin melanomas, cutaneous benign fibrous histiocytomas, intravenous leiomyomatosis, aggressive angiomyxomas, liposarcomas, myxoid liposarcomas, low grade fibromyxoid sarcomas, soft tissue leiomyosarcomas, biphasic synovial sarcomas, soft tissue chondromas, alveolar soft part sarcomas, clear cell sarcomas, desmoplastic small round cell tumours, elastofibromas, Ewing's tumours, extraskeletal myxoid chondrosarcomas, inflammatory myofibroblastic tumours, lipoblastomas, lipoma, benign lipomatous tumours, liposarcomas, malignant lipomatous tumours, malignant myoepitheliomas, rhabdomyosarcomas, synovial sarcomas, squamous cell cancers, subungual exostosis, germ cell tumours in the testis, spermatocytic seminomas, anaplastic (undifferentiated) carcinomas, oncocytic tumours, papillary carcinomas, carcinomas of the cervix, endometrial carcinomas, leiomyoma as well as vulva and/or vagina tumours.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Cell Culture and Reagent

Cancer cell lines (67NR, 168FARN, 4T07 and 4T1) were a kind gift from Jing Yang (Cambridge, Mass.) and MEF (wild-type and LRP−/−) were obtained from Joachim Herz (University of Texas, Dallas). They were cultured in Dulbecco's modified Eagle's medium (DMEM) with 10% fetal bovine serum (FBS). Polyclonal rabbit anti-MMP-9 were obtained from Chemicon, monoclonal mouse anti-PN-1 antibodies were generated in the laboratory (clone 4B3). Recombinant human tPA was obtained from Calbiochem and recombinant human Thrombin from Chromogenix.

Protein Extraction and Western Blot Analysis:

Total cell protein were extracted in radioimmunoprecipitation assay (RIPA) buffer containing 1% NP-40, 1%, Sodium Deoxycholate and 0.1% SDS. To extract protein from tumours, tissues were lysed by sonication in RIPA buffer. Lysates were centrifuged at 4° C. during 20 min at 13000 rpm and supernatant were used for Western blotting on 10% polyacrylamide gels.

Reverse Transcriptase-PCR Analysis

RNA were extracted from cells with RNeasy Kit (Qiagen). 1 μg of RNA was used for Reverse Transcription using oligod (T) and MMLV Reverse transcriptase (Qiagen), according to the manufacturer's instructions.

PCR were performed using the following program: 1 min of denaturation step at 94° C., 1 min of annealing at 55° C. and 1 min of DNA synthesis at 72° C., the numbers of cycles differed from one PCR to the other:

```
PN-1
(forward
5' gcgatataatgtaaacggag-3',        (SEQ ID NO: 1)
and reverse
5'-caaaaattgatggactcagag-3'        (SEQ ID NO: 2))
for 27 cycles PAI-1
(forward
5'-atgagatcagtactgcggatgccatct-3', (SEQ ID NO: 3)
and reverse
5'-gcacagagacggtgctgccatcagact-3'  (SEQ ID NO: 4))
for 36 cycles MMP-9
(forward
5'-cctagtgagagactctacac-3'         (SEQ ID NO: 5)
and reverse
5'-agagccacgaccatacagatac-3'       (SEQ ID NO: 6))
for 32 cycles;

LRP
(forward
5'-acctgcaggtccttgccttg-3'         (SEQ ID NO: 7)
and reverse
5'-caaaggtggagcgctgtgac-3'         (SEQ ID NO: 8))
for 35 cycles Actin
(forward
5'-gtgggccgctctaggcacaa-3'         (SEQ ID NO: 9)
and reverse
5'-ctctttgatgtcacgcacgatttc-3'     (SEQ ID NO: 10))
for 26 cycles.
``` tPA, Thrombin, PN-1, PN-1/tPA, PN-1/Thrombin Complexes Treatments

Cells were seeded on a 48-well plate at density of 50000 cells per well and grown in full serum culture medium. The day after, medium was switched with DMEM/stripped BSA 0.1% containing or not tPA, PN-1 or complex tPA/PN-1 at concentration of 20 nM. tPA/PN-1 complexes were generated by mixing tPA and PN-1 together in DMEM/stripped BSA 0.1% and left at room temperature 15 min before being added to the cells. The same was done for Thrombin complex experiments.

Zymography:

Conditioned media were normalized for protein contents and 15 μg were mixed with equal volume of sample buffer (0.5M Tris-HCl, 20% glycerol, 2% bromophenol blue and 10 percent SDS). Samples were fractioned in 10% polyacrylamide gel containing 1 mg/ml gelatin by electrophoresis. The gels were soaked in 2.5% Triton X-100 for 1 to 2 hours at room temperature to remove SDS and sequentially incubated in incubation buffer (50 mM Tris-HCl, 10 mM CaCl2 pH7.4) overnight at 37° C. to allow gelatinases digestion. Gels were stained with 0.25% Coomassie Brilliant Blue R-250 in 30% Methanol and 10% Acetic Acid and destained with 10% Methanol and 10% Acetic Acid. Gelatinolytic activity appeared as clear bands of digested gelatin against dark blue background of stained gelatin. The intensity of the band at 87 kDa reflects the gelatinolytic activity of MMP-9.

Generation of 4T1 Clones Stably Transfected with shRNA Against Mouse PN-1.

The sequences used to inhibit mouse PN-1 were cloned into pSilencer (Ambion). Target sequences in the mouse PN-1 mRNA were choosed: 1) 5'-ACGGACATTCGTGGCAGGT-3' (SEQ ID NO:11) 2) 5'-GCCGCGTACCTGTCACTAC-3' (SEQ ID NO:12). Oligomers encoding shRNA against these sequences were designed and cloned in the ApaI/EcorV sites of the pSilencer vector according to the manufacturer's instructions.

4T1 cells were co-transfected with each plasmid containing a shRNA and a puromycin vector, pBABE at the ratio 20/1 as described (Gao et al, Biochemical and biophysical Research communications, 321, 2007, 1010-1016). As mock transfected control, 4T1 were also co-transfected with empty pSilencer and pBABE with the same ratio. Colonies resistant to 20 mg/l of puromycin were picked and grown for analysis of PN-1 expression by Western Blot. Over 90, 20 clones showed efficient knock-down of PN-1 protein.

Orthotopic Injection, Metastasis, Tumor Growth.

A total of 500 000 cells in 100 μl were injected into the T4 the mammary fat pad of BALB/c mice using a 1 ml syringe (BD Biosciences). From day 9 to day 26, tumor height (H) and width (W) were measured thrice a week with a caliper and tumor volume was calculated according to the following formula: $H \times \Pi \times (W/2)^2$.

At day 26 post-injection, mice were sacrificed and primary tumor and lungs were dissected. Both lungs were incubated in Bouin solution for 48 hours and washed several times in 70% Ethanol to detect metastases easily as lung tissue is stained in yellow and metastatic foci in white.

Tumor samples were frozen in liquid nitrogen and used for subsequent Western Blotting analyses.

PN-1 Induces Increase of Secreted MMP-9 Level.

PN-1 expression is correlated with secreted MMP-9 production in a model of breast cancer cell lines.

The present inventors used different mouse mammary cell lines displaying different metastatic properties once reinjected in the mouse mammary fat pad. This includes 67NR, 168FARN, 4T07 and 4T1, from the less to the more metastatic. By Western Blot analysis, the present inventors saw that PN-1 was highly expressed in 67NR, 4T07 and 4T1 cells where MMP-9 activity is strong whereas in 168FARN, the less invasive cell line, PN-1 is absent and MMP-9 activity is very low (FIG. 1A), suggesting, without wishing to be bound by theory, that the PN-1 expression pattern is correlated with the activity pattern of MMP-9.

PN-1 Induces Increase of Secreted MMP-9 but not of MMP-9 Expression.

To see if PN-1 could be associated with MMP-9 activity, the present inventors incubated 168FARN, a PN-1 negative cell lines, with 10 µg/ml of recombinant rat PN-1. Zymography analysis of the conditioned media showed that treatment with PN-1 induced an increase in the secreted MMP-9 activity in a dose dependent manner (FIG. 1A). Secreted MMP-9 protein level was shown to be increased after 12 hours of PN-1 treatment by 168FARN cells (FIG. 1B). To determine if the increase of MMP-9 was due to an upregulation of mmp-9 gene expression, the present inventors performed RT-PCR on MMP-9 mRNA analysis of 168FARN treated during different times with PN-1. No significant changes in level of MMP-9 transcript were detected (not shown).

Complex PN-1/Protease is more Potent in Stimulating MMP-9 Increase.

PN-1 as a potent inhibitor of serine protease binds to its target serine protease. To address the ability of complexed PN-1 to increase secreted MMP-9 levels, 168FARN were incubated with complex of protease/PN-1, in that case tPA/PN-1 or thrombin/PN-1 and with protease or PN-1 alone. After zymography analysis on cells conditioned media, the present inventors showed that the complex was more efficient in increasing MMP-9 activity secreted by the cells than protease or PN-1 alone in a statistically significant manner (FIGS. 1C, D).

Increase of Secreted MMP-9 by PN-1 and Complex PN-1/Protease is Mediated Through LRP-1 Receptor.

Complexes of PN-1/protease, once formed, are degraded through LRP-1 scavenger receptor. They bind it with a high affinity whereas serpins (including PN-1 and PAI-1) or protease alone do with much lower affinity. Subsequently, complexes are directed to the lysosomes and degraded whereas the receptor is recycled to the membrane (Knauer et al, 1997, *J Biol Chem.*, 272(19):12261; Knauer et al, 1999, *J Biol Chem.*, 274(1):275, Crisp et al, 2000, *J Biol Chem.*; 275(26):19628; Knauer et al, 2000, *J Biol Chem.*, 275(48):37340; Li et al, 2006, *J Cell Biochem.*, 99(3):936-51).

Recently, LRP-1 was shown to exert signaling activity through tPA binding. Indeed, upon tPA stimulation, LRP is phosphorylated, leading to MAPK phosphorylation and expression of MMP-9 (Hu et al, 2006, *J Biol Chem.*, 27;281(4):2120; Wang et al, 2003, *Nat Med.*, 9(10):1313). To determine if LRP is mediating the effect of the complex on MMP-9, MEF +/+ and MEF LRP-/- were incubated with complex tPA/PN-1, tPA or PN-1 alone. Wild-type cells showed, as expected, an increase of MMP-9 upon treatment, this increase being more important when cells were incubated with complex. However, MEF LRP-/- did not show any changes in secreted MMP-9 by zymography analysis upon treatments, suggesting that LRP-1 is mediating the effect of complex tPA/PN-1 or PN-1 alone (FIG. 2).

Knock-down of PN-1 in Highly Metastatic 4T1 Cell Line Induces Down Regulation of MMP-9 Expression and of Metastatic Properties.

Knock-down of PN-1 Induces Down-regulation of MMP-9 Expression.

In view of the fact that PN-1 was shown to be able to increase MMP-9 secreted by cancer cells and fibroblasts, the present inventors investigated the consequences of PN-1 knock-down in a highly metastatic 4T1 cell line.

4T1 cells were stably transfected with pSilencer that allows expression of shRNA against two different sequences. Two clones, clones 1 and 36, were stably transfected with construct targeting one sequence and clone 22 with construct targeting another one (FIG. 3).

4T1 PN-1 shRNA clones 1, 22 and 36 showed significant knock-down of PN-1, the knock-down in clone 36 being extremely efficient as shown by Western Blot (FIG. 3A) and RT-PCR (FIG. 3B).

4T1 PN-1 shRNA clones 1 and 22 showed that knock-down of PN-1 reduced dramatically the expression of MMP-9 expression, as shown by RT-PCR and zymography, compared to mock transfected 4T1 cells or untransfected cells.

Surprisingly, no downregulation of MMP-9 was detectable in 4T1 PN-1 shRNA clone 36 where PN-1 inhibition was the most effective. RT-PCR analysis showed an upregulation of expression of the homolog PAI-1. Without wishing to be bound by theory, it is postulated that PAI-1 might be responsible of the normal level of MMP-9 in this PN-1 knock-down clones (FIG. 3B). Indeed, PAI-1 was shown to be able to increase MMP-9 activity as PN-1 does (data not shown). To determine if PAI-1 upregulation was mediated by PN-1 knock-down, the present inventors incubated 4T1 PN-1 shRNA clone 36 with recombinant rat PN-1. Addition of recombinant PN-1 in 4T1 PN-1 shRNA clone 36 resulted in a down-regulation of PAI-1 level, suggesting that the upregulation was a consequence of the absence of PN-1, e.g. as a compensatory mechanism (data not shown).

Knock-down of PN-1 Reduces Metastatic Properties of 4T1 Cells.

To evaluate if the PN-1 shRNA-mediated PN-1 downregulation was associated with alterations in 4T1 tumor growth and metastasis, cells were injected into the T4 mammary fat pad of BALB/c mice. Previous studies showed that 4T1 cells undergo spontaneous lung metastasis via intravasation into blood after orthotopic implantation into mammary fat pads (Aslakson et Miller, 1992, *Cancer Res.*, 52: 1399).

Mice were injected with the three 4T1 PN-1 shRNA clones, with mock transfected 4T1 and untransfected 4T1 cells. Frequent measurements of primary tumor from day 9 to day 26 post-injection did not show any significant differences in tumor size with mice injected with mock transfected or untransfected 4T1 (FIG. 4A).

Figures 4A, 4B:
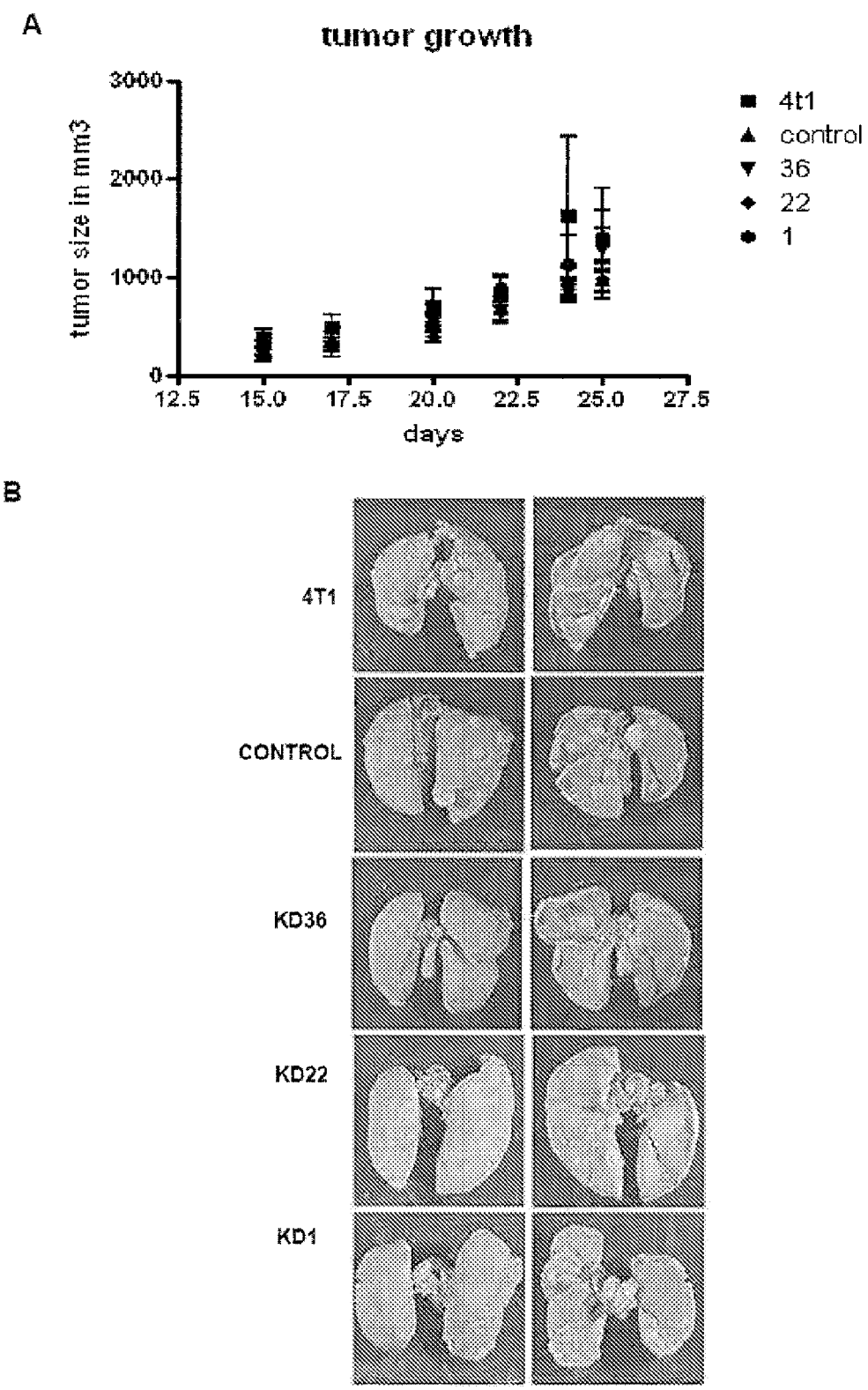
Figure 4C:
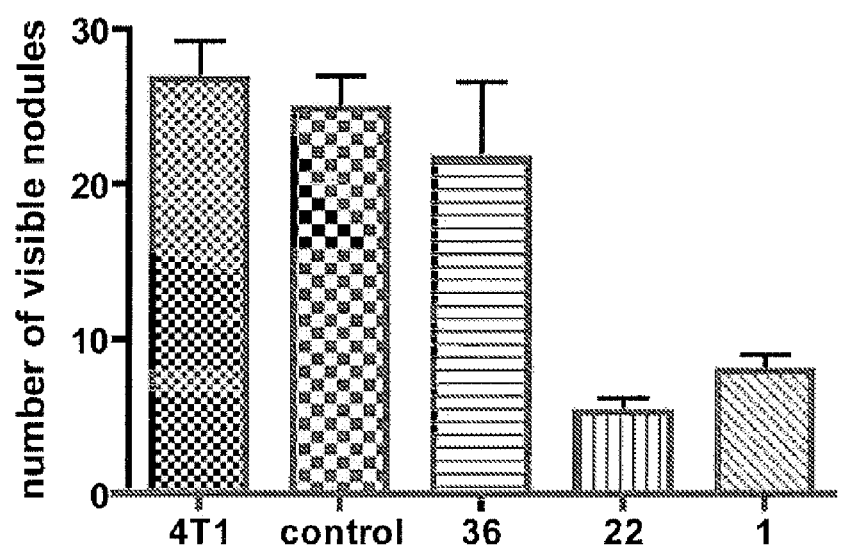

Twenty-six days post injection, lungs from mice injected with 4T1 PN-1 shRNA 1 and 22 showed significantly less metastatic nodules than 4T1 PN-1 shRNA 36, mock transfected and untransfected 4T1 cells (FIGS. 4B and 4C). Without wishing to be bound by theory, the absence of effect of PN-1 shRNA 36 could be due to upregulation of PAI-1, subsequent to the strong down regulation of PN-1, compensating the effect of the missing serpin.

Host-derived PN-1 is Not Essential for 4T1 Tumor Growth or Metastasis.

In addition to tumor cells, fibroblasts, smooth muscle cells and endothelial cells also secrete PN-1 into the stroma. To determine the involvement of host-derived PN-1 in 4T1 primary tumor outgrowth and metastasis, the inventors examined the behavior of the cells in PN-1 null mice, which have a normal life expectancy and no overt phenotype. Parental 4T1 cells were injected into mammary fat pads of wild type and PN-1 null Balb/c mice and tumor outgrowth kinetics and tumor size were monitored. All mice developed primary mammary tumors with the same kinetics. Furthermore, an examination of the lungs revealed similar metastatic efficiency for the 4T1 cells in wild type and PN-1 null animals. In summary, results from the in vivo experiment show that expression of PN-1 in 4T1 tumors is essential for metastatic spread, whereas host-derived PN-1 is not necessary for the process.

In conclusion, PN-1 was shown in the present examples to increase the levels of the pro-invasive secreted MMP-9 by cancer cells. This effect was even enhanced when PN-1 formed complex with one of its targeting protease such as thombin and tPA. Furthermore, the above examples show that PN-1 or complex PN-1/protease exert their effect through binding to LRP-1 receptor.

Morever, the above examples surprisingly show that PN-1 is a very pro-invasive and a pro-metastatic molecule. This was even more unexpected from a serine protease inhibitor known to inhibit tPA, a protease that maturates MMP-9 and upregu-lates of MMP-9 expression (Matrisian et al, 1990, *Trends Genet*, 6(4):121; Birkedal-Hansen et al, 1995, *Curr Opin Cell Biol.*, 7(5):728; Murphy et al, 1995, *Methods Enzymol.*, 248: 470; Hu et al, 2006, *J Biol Chem.*, 281(4):2120; Wang et al, 2003, *Nat Med.*, 9(10):1313). Additionally, PN-1 is also a potent inhibitor of the pro-migratory and pro-invasive protease uPA (Baker et al, 1980, *Biochemistry.*, 26(20):6407; Guenther et al, 1985, *EMBO J.*, 4(8):1963; Stone et al, 1987, *Arch Biochem Biophys.*, 252(1):237).

Finally, in vivo experiments confirm that inhibition of PN-1 in tumor can provide diminution of metastatic nodules, hence providing for a target for therapy. Since its effect is mediated through binding to its receptor LRP in an autocrine loop, especially when complexed with one of its target protease, inhibition of LRP-binding is also a potential target.

The invention claimed is:

1. A method of inhibiting metastasis of a tumor in a subject comprising the administration of an inhibitor of protease nexin-1 (PN-1) to said subject, wherein said inhibitor is administered at a therapeutical dosage that does not completely inhibit the expression and/or activity of PN-1, and wherein the inhibitor is an anti-sense molecule or an interfering molecule, and wherein the anti-sense molecule binds complimentary to PN-1 mRNA.

2. The method of claim 1, wherein the inhibitor and/or its therapeutical dosage does not up-regulate the expression and/or activity of PAI1, and/or wherein the inhibitor and/or its therapeutical dosage leads to a down-regulation of the expression and/or activity of MMP-9.

3. The method of claim 1, wherein the inhibitor and/or its therapeutical dosage inhibits more than 50%, but less than 90%, of the expression and/or activity of PN-1 as compared to the expression and/or activity of PN-1 in the absence of said inhibitor.

4. The method of claim 1 wherein the inhibitor and/or its therapeutical dosage does not up-regulate the expression and/or activity of PAI1, and/or wherein the inhibitor and/or its therapeutical dosage leads to a down-regulation of the expression and/or activity of MMP-9.

5. The method of claim 1 wherein the inhibitor and/or its therapeutical dosage inhibits more than 50%, but less than 90%, of the expression and/or activity of PN-1 as compared to the expression and/or activity of PN-1 in the absence of said inhibitor.

6. The method of claim 1 wherein the potentially metastising cells are breast tumour cells, prostate carcinoma cells or oral squamous carcinoma cells.

7. The method of claim 6, wherein the inhibitor and/or its therapeutical dosage does not up-regulate the expression and/or activity of PAI1, and/or wherein the inhibitor and/or its therapeutical dosage leads to a down-regulation of the expression and/or activity of MMP-9.

8. The method of claim 7, wherein the inhibitor and/or its therapeutical dosage inhibits more than 50 but less than 90%, of the expression and/or activity of PN-1 as compared to the expression and/or activity of PN-1 in the absence of said inhibitor.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Homo sapiens

<400> SEQUENCE: 1
gcgatataat gtaaacggag                                                   20

<210> SEQ ID NO 2
<211> LENGTH: 21
<212> TYPE: DNA
<213> ORGANISM: Homo sapiens

<400> SEQUENCE: 2
caaaaattga tggactcaga g                                                 21

<210> SEQ ID NO 3
<211> LENGTH: 27
<212> TYPE: DNA
<213> ORGANISM: Homo sapiens

<400> SEQUENCE: 3
atgagatcag tactgcggat gccatct                                           27

<210> SEQ ID NO 4
<211> LENGTH: 27
<212> TYPE: DNA
<213> ORGANISM: Homo sapiens

<400> SEQUENCE: 4
gcacagagac ggtgctgcca tcagact                                           27

<210> SEQ ID NO 5
<211> LENGTH: 20
<212> TYPE: DNA
<213> ORGANISM: Homo sapiens

<400> SEQUENCE: 5
cctagtgaga gactctacac                                                   20

<210> SEQ ID NO 6
<211> LENGTH: 22
<212> TYPE: DNA
<213> ORGANISM: Homo sapiens

<400> SEQUENCE: 6
```

-continued

```
agagccacga ccatacagat ac                                          22

<210> SEQ ID NO 7
<211> LENGTH: 20
<212> TYPE: DNA
<213> ORGANISM: Homo sapiens

<400> SEQUENCE: 7
acctgcaggt ccttgccttg                                             20

<210> SEQ ID NO 8
<211> LENGTH: 20
<212> TYPE: DNA
<213> ORGANISM: Homo sapiens

<400> SEQUENCE: 8
caaaggtgga gcgctgtgac                                             20

<210> SEQ ID NO 9
<211> LENGTH: 20
<212> TYPE: DNA
<213> ORGANISM: Homo sapiens

<400> SEQUENCE: 9
gtgggccgct ctaggcacaa                                             20

<210> SEQ ID NO 10
<211> LENGTH: 24
<212> TYPE: DNA
<213> ORGANISM: Homo sapiens

<400> SEQUENCE: 10
ctctttgatg tcacgcacga tttc                                        24

<210> SEQ ID NO 11
<211> LENGTH: 19
<212> TYPE: DNA
<213> ORGANISM: Mus musculus

<400> SEQUENCE: 11
acggacattc gtggcaggt                                              19

<210> SEQ ID NO 12
<211> LENGTH: 19
<212> TYPE: DNA
<213> ORGANISM: Mus musculus

<400> SEQUENCE: 12
gccgcgtacc tgtcactac                                              19
```